(12) United States Patent
Lao et al.

(10) Patent No.: US 9,884,856 B2
(45) Date of Patent: Feb. 6, 2018

(54) CRYSTAL FORM OF DABRAFENIB MESYLATE AND PREPARATION METHOD THEREOF

(71) Applicant: Hangzhou Pushai Pharmaceutical Technology Co., LTD., Hangzhou (CN)

(72) Inventors: Haiping Lao, Hangzhou (CN); Xiaoxia Sheng, Hangzhou (CN); Xiaohong Sheng, Hangzhou (CN)

(73) Assignee: HANGZHOU PUSHAI PHARMACEUTICAL TECHNOLOGY CO., LTD., Hangzhou (CN)

( * ) Notice: Subject to any disclaimer, the term of this patent is extended or adjusted under 35 U.S.C. 154(b) by 0 days.

(21) Appl. No.: 15/247,086

(22) Filed: Aug. 25, 2016

(65) Prior Publication Data
US 2016/0368909 A1   Dec. 22, 2016

Related U.S. Application Data

(60) Division of application No. 14/925,381, filed on Oct. 28, 2015, now Pat. No. 9,453,011, which is a continuation of application No. PCT/CN2014/081549, filed on Jul. 3, 2014.

(30) Foreign Application Priority Data

Jul. 8, 2013 (CN) .......................... 2013 1 0283705

(51) Int. Cl.
*C07D 239/02*  (2006.01)
*C07D 277/04*  (2006.01)
*A61K 31/505* (2006.01)
*A61K 31/425* (2006.01)
*C07D 417/04* (2006.01)

(52) U.S. Cl.
CPC .................................. *C07D 417/04* (2013.01)

(58) Field of Classification Search
None
See application file for complete search history.

(56) References Cited

U.S. PATENT DOCUMENTS 7,994,185 B2   8/2011  Rheault
2016/0046615 A1   2/2016  Lao et al.

FOREIGN PATENT DOCUMENTS

| CN | 102083312 A | 6/2011 |
| WO | WO 2009/137391 A2 | 11/2009 |
| WO | WO 2012/148588 A2 | 11/2012 |
| WO | WO 2014/169770 A1 | 10/2014 |

OTHER PUBLICATIONS

English Translation of the International Search Report and Written Opinion for International Application No. PCT/CN2014/081549, State Intellectual Property Office of the P.R. China, China, dated Oct. 10, 2014, 6 pages.

*Primary Examiner* — Jeffrey S Lundgren
*Assistant Examiner* — Michael Schmitt
(74) *Attorney, Agent, or Firm* — Sterne, Kessler, Goldstein & Fox PLLC

(57) ABSTRACT

The present invention involves novel crystal forms of Dabrafenib mesylate and preparation method thereof, wherein the novel crystal forms are more stable in water or an aqueous system, and have greater solubility and dissolution rate in water, thus having better stability and bioavailability compared with the existing crystal forms.

20 Claims, 9 Drawing Sheets

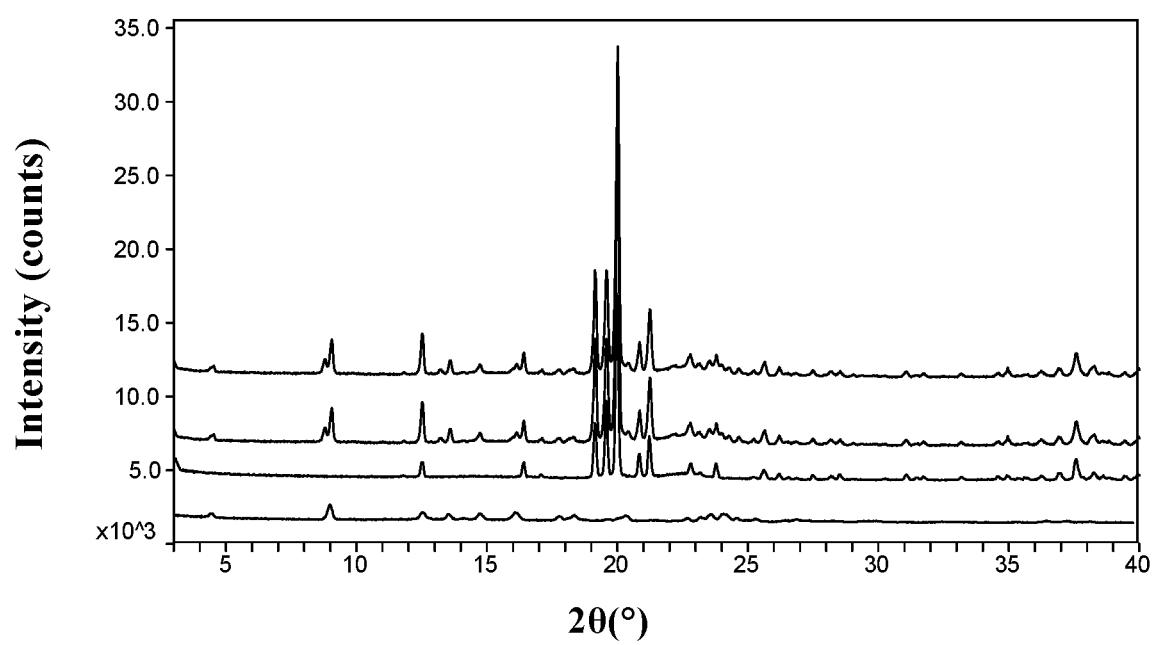
Figuer 17

CRYSTAL FORM OF DABRAFENIB MESYLATE AND PREPARATION METHOD THEREOF

FIELD OF THE INVENTION

The present invention relates to the crystalline forms of a drug compound. To be specific, it relates to the new crystal form of a benzene sulfonamide thiazole methanesulfonate, and its methods of preparation.

BACKGROUND OF THE INVENTION

Dabrafenib is a benzene sulfonamide thiazole compound and is a selective BRAF inhibitor. Results of the Phase I/II clinical trials show Dabrafenib has therapeutic activities and an acceptable safety profile in patients with BRAFV600E-mutan melanoma. The chemical name of Dabrafenib methanesulfonate is N-[3-[5-(2-amino-4-pyrimidinyl)-2-(tert-butyl)-thiazol-4-yl]-2-fluorophenyl]-2,6-difluorobenzene sulfonamide methanesulfonate; the molecular formula: $C_{24}H_{24}F_3N_5O_5S_3$; molecular weight: 615.7; and chemical structure as follows:

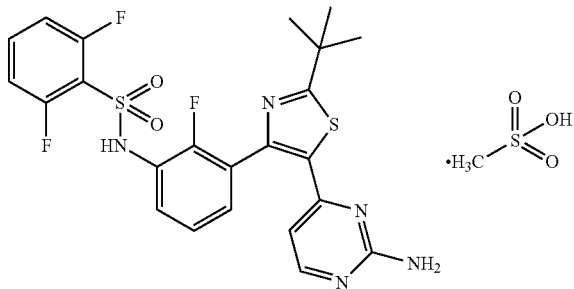

Patent documents WO2009/137391 and CN200980126781.6 (incorporated into the present application by reference) disclosed identification, preparing process and uses of Dabrafenib methanesulfonate. To be specific, examples 58d and 58e disclosed Dabrafenib methanesulfonate and its preparation methods, and provided its $^1$HNMR data, but did not provide characterization data in relation to its physical state. Moreover, the patent documents also disclosed that Dabrafenib methanesulfonate exhibited inhibitory effects on one or more Raf-family kinases.

In addition, patent document WO2012/148588A2 (incorporated into the present application by reference) disclosed Raman, XRPD and DSC/TGA analytical data of Dabrafenib methanesulfonate that was mentioned in WO2009/137391. For convenience, the crystal form prepared according to examples 58d and 58e in WO2009/137391 and CN200980126781.6 hereinafter is referred as to "the Known Crystal Form I".

In the present research, it was discovered that the Known Crystal Form I has the following defects: it readily converts to free base in water or other aqueous system(s), thus unable to maintain its original crystalline form. In pharmaceutical processes, this change may result in changes in nature and bioavailabilities of formulations.

Therefore, there is a need to discover new crystal forms of Dabrafenib methanesulfonate with good purity, improved thermodynamic stability in water or aqueous system(s) and better suitability for the pharmaceutical application.

SUMMARY OF THE INVENTION

In view of the defects in the prior art, the purpose of the present invention is mainly to provide new crystal forms of Dabrafenib methanesulfonate with improved stability in water or in aqueous system(s), and to provide their preparation methods.

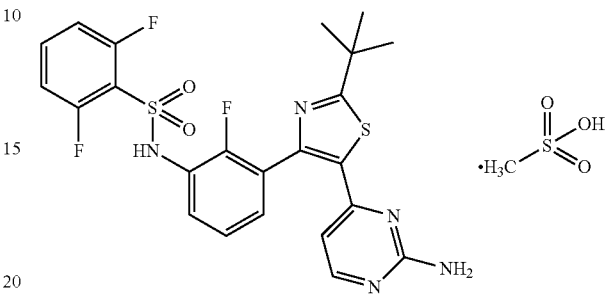

According to the purpose of the present invention, Crystal Form IV of Dabrafenib methanesulfonate (hereinafter referred to as Crystal Form IV) and its preparation methods are provided. Crystal Form VI is a hydrate. Preferably, per mole of Dabrafenib methanesulfonate contains about 1.5 mole of water.

Measured using Cu—Kα radiation, Crystal Form IV is characterized by a X-ray powder diffraction pattern having the characteristic peaks at diffraction angles 2θ of 4.7±0.2°, 9.2±0.2°, 12.8±0.2°, 13.8±0.2°, 15.0±0.2° and 16.3±0.2°.

In one preferred embodiment of the present invention, Crystal Form IV is characterized by a X-ray powder diffraction pattern having the characteristic peaks at the diffraction angles 2θ of 4.7±0.2°, 9.2±0.2°, 12.8±0.2°, 13.8±0.2°, 15.0±0.2°, 16.3±0.2°, 18.0±0.2°, 18.6±0.2°, 20.6±0.2°, 22.9±0.2°, 23.8±0.2° and 24.3±0.2°.

In the further preferred embodiment of the present invention, Crystal Form IV is characterized by a X-ray powder diffraction pattern having the following characteristic peaks at the diffraction angles 2θ and their relative intensities:

| Diffraction angle (2θ) | Relative intensity (%) |
|---|---|
| 4.7 ± 0.2° | 25.5 |
| 9.2 ± 0.2° | 100.0 |
| 12.8 ± 0.2° | 46.1 |
| 13.8 ± 0.2° | 34.2 |
| 15.0 ± 0.2° | 40.3 |
| 16.3 ± 0.2° | 49.3 |
| 18.0 ± 0.2° | 25.4 |
| 18.6 ± 0.2° | 34.7 |
| 20.6 ± 0.2° | 32.9 |
| 22.9 ± 0.2° | 18.6 |
| 23.4 ± 0.2° | 16.5 |
| 23.8 ± 0.2° | 41.5 |
| 24.3 ± 0.2° | 41.0 |
| 24.8 ± 0.2° | 11.8 |
| 25.6 ± 0.2° | 11.5 |
| 27.1 ± 0.2° | 16.1. |

Not limited, in one specific embodiment of the present invention, the X-ray powder diffraction pattern of Crystal Form IV is shown in FIG. 1.

Crystal Form IV has at least one of the following properties:

The differential scanning calorimetry (DSC) thermogram of Crystal Form IV shows: the sample has a broad and large endothermic peak (the solvent peak) at 15° C.~105° C., a melting range of 132° C.~148° C. for the dehydrated sample, followed by an exothermic phase transformation peak at 200° C.~245° C., and finally a melting peak at 249° C.

Crystal Form IV has the following beneficial properties:

1) It is stable when stored for 1 month at room temperature, or at room temperature and 97% RH, 2) The Known Crystal Form I converts to its free base monohydrate when slurried for 15 minutes in water, while Crystal Form IV still remains its Crystal Form IV of methanesulfonate when slurried for 15 minutes in water, and then converts to its free base monohydrate after overnight stirring. This indicates that Crystal Form IV is better in keeping the sample in the state of methanesulfonate that has higher solubility than that of free base. Crystal Form IV has better stability in water or aqueous system(s).

3) Comparing the dissolution quantity of 0~22 h, the dissolution quantity of Crystal Form IV is larger than that of the Known Crystal Form I at any test point. This indicates that Crystal Form IV has better solubility and bioavailabilty.

4) Comparing the dissolution quantity of 0~120 min, the dissolution quantity of Crystal Form IV capsule is larger than that of the Known Crystal Form I capsule at any test point. This indicates that Crystal Form IV capsule has higher dissolution rate.

Crystal Form IV may be prepared by any one of the following preparation methods

1) Dissolving the Known Crystal Form I of Dabrafenib methanesulfonate in a mixed solution of methanol and tetrahydrofuran, evaporating to recrystallize, then separating and drying the precipitated crystals to get Crystal Form IV;

The volume ratio of methanol to tetrahydrofuran is 0.1:1~100:1, preferably, 0.5:1~50:1, more preferably, 0.5:1~5:1;

2) Dissolving the Known Crystal Form I of Dabrafenib methanesulfonate in acetone, evaporating to crystallize, then separating and drying the precipitated crystals to get Crystal Form IV;

3) Dissolving the Known Crystal Form I of Dabrafenib methanesulfonate in isopropanol, adding polyacrylic acid, evaporating to crystallize, then separating and drying the precipitated crystals to get Crystal Form IV;

The amount of the polyacrylic acid is 0.1 wt %~10 wt % of that of the Known Crystal Form I, preferably 0.5 wt %~10 wt %, more preferably 2 wt %~5 wt %; The average formula weight of the polyacrylic acid is 2,000-5,000.

In the above three preparation methods, the amount of the Known Crystal Form I of Dabrafenib methanesulfonate is 0.1~1 times of its solubility in the corresponding solution at room temperature, preferably, 0.5~1 times, and more preferably, 0.8~1 times;

The crystallizing temperature is room temperature to 40° C., preferably, room temperature; the duration of crystallizing is 1~14 days, preferably, 2 days;

The drying may be conducted at reduced pressure or normal pressure; preferably, pressure<0.09 Mpa; The temperature is 30° C.~120° C., preferably, 40° C.~80° C., and more preferably, 40° C.~60° C.; the duration is 10~72 hours, preferably, 10~48 hours, and more preferably, 10~24 hours;

4) Storing the Crystal Form II or the Crystal Form V of Dabrafenib methanesulfonate to get Crystal Form IV;

The temperature of storage is room temperature to 40° C., preferably, room temperature; the duration of storage is 15 minutes~7 days, preferably, 1 day;

5) Heating the Crystal Form II of Dabrafenib methanesulfonate to 120° C., and then naturally cool it to room temperature to get Crystal Form IV;

The rate of heating is 5° C.~15° C./minute, preferably, 10° C./minute;

For example, the heating method is TGA-programmed heating.

According to the purpose of the present invention, Crystal Form II of Dabrafenib methanesulfonate (hereinafter referred to as Crystal Form II) and its preparation methods are provided. Crystal Form II is a hydrate; Preferably, per mole of Dabrafenib methanesulfonate contains about 2 mole of water.

Measured using Cu—Kα radiation, Crystal Form II is characterized by a X-ray powder diffraction pattern having the characteristic peaks at diffraction angles 2θ of 4.7±0.2°, 9.3±0.2°, 13.9±0.2°, 15.4±0.2°, 17.0±0.2° and 19.0±0.2°.

In one preferred embodiment of the present invention, Crystal Form II is characterized by a X-ray powder diffraction pattern having the characteristic peaks at diffraction angles 2θ of 4.7±0.2°, 9.3±0.2°, 12.9±0.2°, 13.9±0.2°, 15.4±0.2°, 17.0±0.2°, 17.9±0.2°, 18.5±0.2°, 19.0±0.2°, 20.5±0.2°, 23.6±0.2° and 24.8±0.2°.

In the further preferred embodiment of the present invention, Crystal Form II is characterized by a X-ray powder diffraction pattern having the following characteristic peaks at diffraction angles 2θ and their relative intensities:

| Diffraction angle (2θ) | Relative intensity (%) |
|---|---|
| 4.7 ± 0.2° | 29.2 |
| 9.3 ± 0.2° | 100.0 |
| 12.4 ± 0.2° | 20.9 |
| 12.9 ± 0.2° | 30.1 |
| 13.9 ± 0.2° | 32.1 |
| 14.5 ± 0.2° | 19.0 |
| 15.4 ± 0.2° | 35.3 |
| 16.3 ± 0.2° | 26.5 |
| 17.0 ± 0.2° | 18.9 |
| 17.9 ± 0.2° | 34.8 |
| 18.5 ± 0.2° | 36.8 |
| 19.0 ± 0.2° | 27.0 |
| 19.7 ± 0.2° | 14.9 |
| 20.5 ± 0.2° | 45.3 |
| 22.6 ± 0.2° | 14.9 |
| 23.6 ± 0.2° | 49.1 |
| 24.1 ± 0.2° | 33.3 |
| 24.8 ± 0.2° | 40.9 |
| 26.5 ± 0.2° | 18.7 |
| 27.3 ± 0.2° | 12.5 |
| 27.8 ± 0.2° | 19.6 |
| 28.9 ± 0.2° | 13.5 |
| 37.4 ± 0.2° | 15.6. |

Not limited, in one specific embodiment of the present invention, the X-ray powder diffraction pattern of Crystal Form II is shown in FIG. 6.

Crystal Form II can be prepared by the following method, comprising:

Suspending the Crystal Form IV of Dabrafenib methanesulfonate in water to form a suspension, agitating to recrystallize, and then separating the precipitated crystals without drying to get Crystal Form II;

The amount of the Crystal Form IV of Dabrafenib methanesulfonate is 1.1~20 times of its solubility in water at room temperature, preferably, 1.5~10 times, and more preferably, 2~5 times;

The recrystallizing temperature is room temperature to 40° C., preferably, room temperature; the duration of recrystallizing is 0.5~25 minutes, preferably, 1~15 minutes.

According to the purpose of the present invention, Crystal Form III of Dabrafenib methanesulfonate (hereinafter referred to as Crystal Form III) and its preparation methods are provided.

Measured using Cu—Kα radiation, Crystal Form III is characterized by a X-ray powder diffraction pattern having the characteristic peaks at the diffraction angles 2θ of 4.2±0.2°, 8.6±0.2°, 13.2±0.2°, 14.5±0.2°, 17.4±0.2° and 19.5±0.2°.

In one preferred embodiment of the present invention, Crystal Form III is characterized by a X-ray powder diffraction pattern having the characteristic peaks at the diffraction angles 2θ of 4.2±0.2°, 8.6±0.2°, 12.4±0.2°, 13.2±0.2°, 14.5±0.2°, 17.4±0.2°, 18.0±0.2°, 18.6±0.2°, 19.5±0.2°, 20.1±0.2°, 24.7±0.2° and 25.1±0.2°.

In the further preferred embodiment of the present invention, Crystal Form III is characterized by a X-ray powder diffraction pattern having the following characteristic peaks at the diffraction angles 2θ and their relative intensities:

| Diffraction angle (2θ) | Relative intensity (%) |
|---|---|
| 4.2 ± 0.2° | 25.5 |
| 8.6 ± 0.2° | 100.0 |
| 9.6 ± 0.2° | 20.7 |
| 12.4 ± 0.2° | 30.5 |
| 13.2 ± 0.2° | 90.5 |
| 14.5 ± 0.2° | 52.4 |
| 16.4 ± 0.2° | 21.5 |
| 17.4 ± 0.2° | 41.5 |
| 18.0 ± 0.2° | 26.5 |
| 18.6 ± 0.2° | 33.1 |
| 19.5 ± 0.2° | 59.3 |
| 20.1 ± 0.2° | 45.1 |
| 21.8 ± 0.2° | 17.5 |
| 23.2 ± 0.2° | 21.1 |
| 24.7 ± 0.2° | 44.4 |
| 25.1 ± 0.2° | 33.8 |
| 28.7 ± 0.2° | 22.5. |

Not limited, in one specific embodiment of the present invention, the X-ray powder diffraction pattern of Crystal Form III is shown in FIG. 8.

Crystal Form III can be prepared by the following method, comprising: Dissolving the Known Crystal Form I of Dabrafenib methanesulfonate in a mixed solvent of methanol and an organic solvent, evaporating to crystallize, then separating the precipitated crystals, without drying to get Crystal Form III;

The organic solvent is selected from the group consisting of ethyl ether, ethyl acetate, butanone and C4-alkanol; the C4-alkanol includes n-butanol and sec-butyl alcohol;

The amount of the Known Crystal Form I of Dabrafenib methanesulfonate is 0.1~1 times of its solubility in the mixed solvent at room temperature, preferably, 0.5~1 times, and more preferably, 0.8~1 times;

The volume ratio of methanol to the organic solvent is 0.1:1~100:1, preferably, 0.5:1~50:1, more preferably, 0.5:1~5:1;

The crystallization temperature is room temperature to 40° C., preferably, room temperature; the duration of crystallization is 1~60 minutes, preferably, 10 minutes.

According to the purpose of the present invention, Crystal Form V of Dabrafenib methanesulfonate (hereinafter referred to as Crystal Form V) and its preparation methods are provided. Crystal Form VI is an anhydrate.

Measured using Cu—Kα radiation, Crystal Form V is characterized by a X-ray powder diffraction pattern having the characteristic peaks at the diffraction angles 2θ of 8.9±0.2°, 14.8±0.2°, 15.8±0.2°, 16.7±0.2°, 17.9±0.2° and 19.0±0.2°.

In one preferred embodiment of the present invention, Crystal Form V is characterized by a X-ray powder diffraction pattern having the characteristic peaks at the diffraction angles 2θ of 8.9±0.2°, 14.8±0.2°, 15.1±0.2°, 15.8±0.2°, 16.7±0.2°, 17.9±0.2°, 19.0±0.2°, 23.8±0.2°, 25.5±0.2°, 31.1±0.2° and 36.1±0.2°.

In the further preferred embodiment of the present invention, Crystal Form V is characterized by a X-ray powder diffraction pattern having the following characteristic peaks at the diffraction angles 2θ and their relative intensities:

| Diffraction angle (2θ) | Relative intensity (%) |
|---|---|
| 8.9 ± 0.2° | 100.0 |
| 14.8 ± 0.2° | 31.7 |
| 15.1 ± 0.2° | 10.2 |
| 15.8 ± 0.2° | 35.6 |
| 16.7 ± 0.2° | 15.5 |
| 17.9 ± 0.2° | 31.7 |
| 19.0 ± 0.2° | 29.2 |
| 23.8 ± 0.2° | 25.3 |
| 25.5 ± 0.2° | 20.2 |
| 31.1 ± 0.2° | 65.0 |
| 36.1 ± 0.2° | 28.7. |

Not limited, in one specific embodiment of the present invention, the X-ray powder diffraction pattern of Crystal Form V is shown in FIG. 9.

Crystal Form V can be prepared by the following method, comprising: Storing the Crystal Form IV of Dabrafenib methanesulfonate at a high temperature for a period of time to get the Crystal Form V;

The high temperature is 40° C.~120° C., preferably, 40° C.~80° C., and more preferably, 60° C.~80° C.; the duration of storage is 0.1~2 hours, preferably, 0.1~1 hours, and more preferably, 0.2~0.5 hours.

In the preparation methods of Crystal Form II, Crystal Form III, Crystal Form IV and Crystal Form V:

The above mentioned "Seperating" is usually accomplished by centrifugation. The operation of "centrifugation" is as follows: placing the sample to be separated into a 2 ml-centrifugal tube and centrifuge it at 6,000 rpm until all the solids settle down at the bottom of the centrifugal tube.

In the present application, the sonication operation is as follows: placing the container in the ultrasonic cleaner at room temperature and treat it for 1~30 minutes at the working power of 20 Khz-40 Khz.

The present invention relates to the new Crystal Form II, Crystal Form III, Crystal Form IV and Crystal Form V of Dabrafenib methanesulfonate.

The Dabrafenib free base hydrate in the present invention is obtained by the followings: Placing the solid obtained in the example 58b of patent documents WO2009/137391 or CN200980126781.6 in water to form a suspension, stirring to crystallize for one week, separating the solids by centrifugation, drying the solids in vacuum for 16 h at 40° C. to get a Dabrafenib free base hydrate. It is confirmed by TGA as a monohydrate and its XRPD is consistent with that of the patent application PCT/CN2014/074883.

Experimental methods may be operated at room temperature or close to room temperature. This means that the experiment is conducted at a condition that is the same as or closes to room temperature or fume hood temperature. Generally this temperature is 10° C.~30° C.

Experimental methods or steps may be operated "overnight". This means that the experiments run overnight during which experimental phenomena are not observed actively. Such period may be 8~22 h, or 10~18 h; generally 16 h.

Unless otherwise specified, the crystal forms mentioned in the present invention may undergo the step of "drying". "Drying" may be conducted in a fume hood, a forced air drying oven or a vacuum drying oven.

Unless otherwise specified, the "anhydrate" mentioned in the present invention refers to the crystal form with its water content no more than 1.5% (by weight) or 1.0% (by weight) measured by TGA.

Crystallization/crystallizing methods in the present invention include evaporation, polymer template method and slurry.

Evaporation means, for example, placing the clear solution of the sample in an uncovered 5 mL-vial and evaporating at a specific temperature (generally at room temperature). Nitrogen purging may be used or evaporation directly at room temperature.

Polymer template method means that, in evaporation experiments, polymer compound(s), which are insoluble in such solvent condition, are added to the solution. The content of polymer compounds is 0.1~10% of that of the sample.

Slurry means, stirring the supersaturated solution (with the presence of insoluble solids) of the sample in different solvent systems to recrystallize, generally for 0.5~60 minutes.

By providing the new Crystal Form IV in the present invention, the problems of crystal form in the prior art have been solved. Compared with the known crystal form, the new crystal forms have one or more beneficial properties, in particular the following advantages: better stability, higher solubility and dissolution rate in water or in aqueous system(s).

In some embodiments, by providing the new Crystal Form II, Crystal Form III, Crystal Form IV or Crystal Form V in the present invention, the problems of crystal form in the prior art have been solved. The new crystal forms have at least one of beneficial properties: better thermodynamic stability and better storage stability.

The examples of the X-ray powder diffraction pattern of Crystal Form II are substantially consistent with that of FIG. 6. The examples of the X-ray powder diffraction pattern of Crystal Form III are substantially consistent with that of FIG. 8. The examples of the X-ray powder diffraction pattern of Crystal Form IV are substantially consistent with that of FIG. 1. The examples of the X-ray powder diffraction pattern of Crystal Form V are substantially consistent with that of FIG. 9.

Generally, Crystal Form II, Crystal Form III, Crystal Form IV, and Crystal Form V substantially do not contain the Known Crystal Form I, in particular, these crystal forms have no characteristic peaks of the Known Crystal Form I at the diffraction angles 2θ of 6.3°, 10.6°, 15.2°, 16.5°, 18.8°, 20.8° and 22.2°.

In addition, the present invention provides a pharmaceutical composition, which comprises a therapeutically and/or preventively effective amount of one or more selected forms, including Crystal Form IV, Crystal Form II, Crystal Form III or Crystal Form V of Dabrafenib methanesulfonate of the present invention, and at least a pharmaceutically acceptable excipient. Moreover, the pharmaceutical composition may also comprise other pharmaceutically acceptable crystal forms or the amorphous form of Dabrafenib or its salts, and such crystal forms include but not limited to the Known Crystal Form I of Dabrafenib methanesulfonate. Optionally, the pharmaceutical composition may also comprise one or more of other active pharmaceutical ingredients, such as any chemical treatment drugs having the activity to treat susceptible tumors.

The above pharmaceutical compositions may be prepared in certain dosage forms and be administered by suitable routes, such as oral, parenteral (including subcutaneous, intramuscular, intravenous or intradermal), rectal, transdermal, nasal, vaginal, etc. The suitable pharmaceutical dosage forms for oral route include tablets, capsules, granules, pulvis, pills, powders, pastilles, solutions, syrups, suspensions, etc, which, according to the actual demand, may be suitable for rapid release, delayed release or adjustable release of active pharmaceutical ingredients. The suitable pharmaceutical dosage forms for parenteral routes include aqueous or non-aqueous sterile injectable solutions, emulsions or suspensions. The suitable pharmaceutical dosage forms for rectal routes include suppository or enema. The suitable pharmaceutical dosage forms for transdermal routes include ointments, creams and patches. The suitable pharmaceutical dosage forms for nasal routes include aerosols, sprays and nasal drops. The suitable pharmaceutical dosage forms for vaginal routes include suppository, plug agents, gels, pastes or sprays. Preferably, the above pharmaceutical compositions may be prepared in the forms of tablets, suspensions, capsules, disintegrating tablets, immediate release tablets, slow release tablets and controlled release tablets; and more preferably, tablets and capsules.

In the above pharmaceutical compositions, the pharmaceutically acceptable excipients in an oral solid form, include but not limited to: diluents, such as starch, pregelatinized starch, lactose, powdered cellulose, microcrystalline cellulose, dicalcium phosphate, tricalcium phosphate, mannitol, sorbitol, and sugar; binders, such as Arabia gum, guar gum, gelatin, polyvinylpyrrolidone, hydroxypropyl cellulose, hydroxypropyl methylcellulose, and polyethylene glycol; disintegrants, such as starch, sodium starch glycolate, pregelatinized starch, cross-linked polyvinylpyrrolidone, cross-linked sodium carboxymethylcellulose, and colloidal silicon dioxide; lubricants, such as stearic acid, magnesium stearate, zinc stearate, sodium benzoate, and sodium acetate; flow aids, such as colloidal silicon dioxide; complex-forming agents, such as cyclodextrins and resins of various grades; release rate controlling agents, such as hydroxypropyl cellulose, carboxymethyl cellulose, hydroxypropyl methyl cellulose, ethyl cellulose, methyl cellulose, methyl methacrylate, and wax. The other useable pharmaceutically acceptable excipients include but not limited to film-forming agent, plasticizer, coloring agent, flavoring agent, viscosity regulator, preservative and antioxidant, etc. Optionally, tablets are coated with the coating layer; for example, shellac isolating coating, sugar coating or polymer coating. The coating layer may contain polymers such as hydroxypropyl methyl cellulose, polyvinyl alcohol, ethyl cellulose, methyl acrylic polymer, hydroxypropyl cellulose or starch, and may also contain antiadherents, such as silica, talcum powder; opacifying agents, such as titanium dioxide; colorants, such as iron oxide. In case of the oral liquid form, the suitable excipients include water, oils, alcohol, glycol, flavoring agents, preservatives, stabilizers and colorants. The aqueous or non-aqueous sterile suspensions may contain suspending agents and thickeners. The suitable excipients for the aqueous suspension include synthetic gum or natural gum, such as Arabia gum, Cocklebur gum, alginate, glucan, sodium carboxymethyl cellulose, methyl cellulose, polyvinyl pyrrolidone or gelatin. In case of parenteral route dosage forms, the excipients in aqueous or non-aqueous sterile injection solutions generally are sterile water, saline or glucose in water, and may contain buffering agent, antioxidant, antibacterial agent, and the solutes which enable the pharmaceutical composition to be isotonic with blood, etc. Each excipient must be acceptable, be compatible with the other ingredients in the formula and harmless to patients.

The mentioned pharmaceutical composition may be in solid state or in liquid state. If the pharmaceutical composition is in a liquid state, then one or more of the above crystal forms may maintain in a solid state in such liquid composition, e.g. as a suspension.

The pharmaceutical composition may be prepared by technicians in this field using the known methods in the prior art. When preparing the pharmaceutical composition, mix Crystal Form IV, Crystal Form II, Crystal Form III or Crystal Form V of Dabrafenib methanesulfonate of the present invention with one or more pharmaceutically acceptable excipients, and optionally, mix with one or more of other active pharmaceutical ingredients. For example, tablets, capsules and granules may be prepared with such technologies as mixing, granulation, tableting, capsule filling, etc; powders may be prepared by mixing the active pharmaceutical ingredients with excipients which are all pulverized to suitable size; solutions and syrups may be prepared by dissolving the active pharmaceutical ingredients in the appropriately flavored water or aqueous solution; suspensions may be prepared by dispersing active pharmaceutical ingredients in the pharmaceutically acceptable carriers.

In addition, the present invention provides uses of Crystal Form IV, Crystal Form II, Crystal Form III or Crystal Form V of Dabrafenib methanesulfonate of the present invention in the manufacture of drugs for inhibiting one or more Raf-family kinases.

In addition, the present invention provides a method of treating and/or preventing diseases associated with one or more Raf-family kinases, which comprising administering to a patient in need thereof a therapeutically and/or preventively effective amount of Crystal Form IV, Crystal Form II, Crystal Form III or Crystal Form V of Dabrafenib methanesulfonate or the pharmaceutical composition containing Crystal Form IV, Crystal Form II, Crystal Form III or Crystal Form V of Dabrafenib methanesulfonate. The patients include but not limited to mammals, such as humans.

The diseases associated with one or more Raf-family kinases include but not limited to susceptible tumors. The specific categories of susceptible tumors can refer to patent documents WO2009/137391 or U.S. Pat. No. 7,994,185. The term "Susceptible Tumors" refers to the tumors which are susceptible to the treatment by kinase inhibitors, especially the tumors which are susceptible to the treatment by Raf inhibitors. The tumors associated with inappropriate activity of one or more Raf-family kinases, and particularly the tumors which exhibit the mutation of the Raf-family kinases, the overexpression of the Raf-family kinases, the mutation of the upstream activators of the Raf-family kinases, or the overexpression of the upstream activators of the Raf-family kinases, and are therefore susceptible to the treatment by Raf inhibitors are known in the prior art, including primary and metastatic tumors and cancers. The specific examples of susceptible tumors include but not limited to: Barret's adenocarcinoma; billiary tract carcinoma; breast cancer; cervical carcinoma; cholangiocarcinoma; central nervous system tumors including primary CNS tumors such as glioblastoma, astrocytoma and ependymal cell tumor, and secondary CNS tumors (i.e. metastatic tumor of central nervous system originating from the outside of central nervous system); colorectal cancer, including colon cancer; gastric carcinoma; head and neck cancer including head and neck squamous cell carcinoma; hematological cancer including leukemia and lymphoma such as acute lymphocytic leukemia, acute myeloid leukemia, myelodysplastic syndrome, chronic myeloid leukemia, Hodgkin's lymphoma, non Hodgkin's lymphoma, megakaryocytic leukemia, multiple myeloma and erythroleukemia; hepatocellular carcinoma; lung cancer including small cell lung cancer and non-small cell lung cancer; ovarian cancer; endometrial carcinoma; pancreatic cancer; pituitary adenoma; prostate cancer; renal carcinoma; sarcoma; skin cancer including melanoma; and thyroid carcinoma.

BRIEF DESCRIPTION OF THE FIGURES

FIG. 17 is the X-ray powder diffraction comparison patterns of Crystal Form IV of the present invention at every stage in Experimental Example 2, wherein, the samples from top to bottom are: the sample obtained from wet granulation (not including the Step 3 of compressing tablets) of Crystal Form IV as API, the sample obtained from physically mixing Crystal Form IV and the excipients at ratios per the formulation, the sample obtained from physically mixing lactose monohydrate and microcrystalline cellulose at ratios per the formulation, and Crystal Form IV).

DETAILED DESCRIPTION OF EMBODIMENTS

Figure 1:
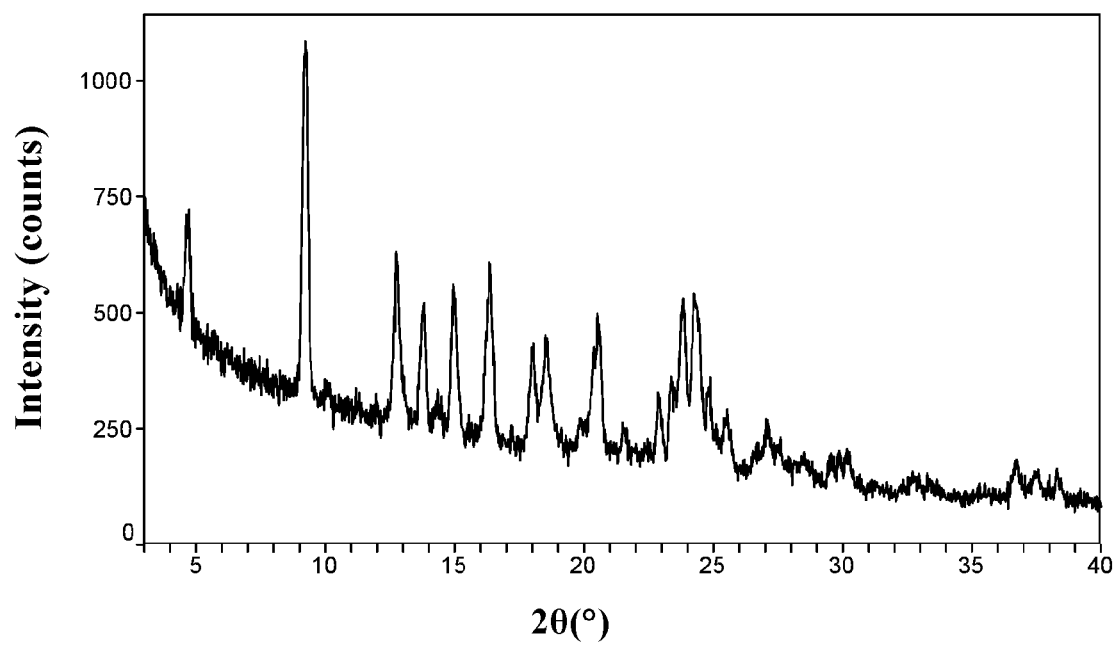
FIG. 1 is the X-ray powder diffraction pattern of Crystal Form IV of the present invention.

The present invention is defined with further reference to the following examples, which describe the preparation and usage of the crystal forms in the present invention in details. It is obvious to the technicians in this field that various changes in materials and methods may be embodied without deviating from the scope of the present invention.

Instruments and Methods Used for Data Collection

The instrument for X-ray powder diffraction (XPRD) is Bruker D8 Advance diffractometer, which equips θ-2θ goniometer, Mo monochromator and Lynxeye detector. The acquisition software is Diffrac Plus XPRD Commander. Prior to use, the instrument is calibrated with the standard substance (generally corindon) attached. The testing conditions are: range of scanning angle 2θ: 3~40°; step size: 0.02°; speed: 0.2 s/step. The testing processes are: Use the Cu Kα X-ray with 1.54 nm in wavelength, under the operation conditions of 40 kV and 40 mA, the sample is examined at room temperature, and place the test sample on sample holder. Unless otherwise specified, samples are not ground before examining.

The Differential Scanning calorimeter (DSC) data are collected by TA Instruments Q200 MDSC; the instrument control software is Thermal Advantage and the analysis software is Universal Analysis. Generally, take 1~10 mg of the sample and place it in an uncovered (unless otherwise specified) aluminum pan and under the protection of 50 mL/min dry $N_2$, heat the sample from room temperature to 275° C. at the heating rate of 10° C./min; and heat changes of the sample during the course are recorded by TA software simultaneously. In the present application, the melting point is reported based on DSC onset temperature.

The thermogravimetric analysis (TGA) data are collected by TA Instruments Q500 TGA; the instrument control software is Thermal Advantage and the analysis software is Universal Analysis. Generally, take 5~15 mg sample and place it in a platinum pan, adopt the segmental high-resolution testing mode, and under the protection of 50 mL/min dry $N_2$, heat the sample from room temperature to 350° C. at the heating rate of 10° C./min, the weight changes of the sample during the course are recorded by TA software simultaneously.

The dynamic vapor sorption analysis (DVS) data are collected by TA Instruments Q5000 TGA; the instrument control software is Thermal Advantage and the analysis software is Universal Analysis. Generally, take 1~10 mg of the sample and place it in a platinum pan, and the weight changes of the sample are recorded during the course of the relative humidity changing from 0% to 80% and then to 0%. According to the specifics of the samples, different adsorption and desorption steps may be used.

The proton nuclear magnetic resonance spectroscopy ($^1$HNMR) data are collected by Bruker Avance II DMX 400M HZ NMR spectrometer. Weigh 1-5 mg of the sample, dissolve it with 0.5 mL DMSO-d6 to get a 2 mg/mL-10 mg/mL solution.

The analysis data of high performance liquid chromatography (HPLC) are collected by Agilent 1260 with the chemical working station of B.04. The corresponding HPLC parameters in this research are: chromatographic column SB-C18 250×4.6 mm 5 μm; column temperature 35° C.; flow rate 0.6 mL/min; flow phase as shown below; wavelength 254 nm; sample inject volume 20 μl; operation time 30 min.

| Time (minutes) | Mobile phase A % (ultrapure water) | Mobile phase B % (acetonitrile) |
|---|---|---|
| 0 | 70 | 30 |
| 3 | 70 | 30 |
| 18 | 10 | 90 |
| 23 | 10 | 90 |
| 28 | 70 | 30 |

Unless otherwise specified, all the Examples are operated at room temperature, the range of temperature is 10° C.~30° C.

The ultrasonic operation is: keep the ultrasonic treatment for 5 minutes at the power of 40 Khz.

Preparation Example 1

The Preparation of the Known Crystal Form I

Refer to the preparation method described in example 58a and 58d of patent documents WO2009/137391 or CN200980126781.6, with the details as follows:

Add N-{3-[5-(2-chloro-4-pyrimidinyl)-2-(1,1-dimethylethyl)-1,3-thiazol-4-yl]-2-fluorophenyl}-2,6-difluorobenzenesulfonamide (196 mg, 0.364 mmol) and 7M methanol solution of ammonia (8 mL 56 mmol) into a 25 mL autoclave, heat to 90° C. and react for 24 h; when the TLC shows complete reaction of the raw material, cool the above reaction system to room temperature, concentrate the solvent to dryness, then treat the residues by the column chromatography to get 90 mg N-{3-[5-(2-amino-4-pyrimidinyl)-2-(1,1-dimethylethyl)-1,3-thiazol-4-yl]-2-fluorophenyl}-2,6-difluorobenzenesulfonamide, yield: 45%.

Add methylsulfonic acid (0.131 ml, 0.393 mmol) into the isopropanol solution of N-{3-[5-(2-amino-4-pyrimidinyl)-2-(1,1-dimethylethyl)-1,3-thiazol-4-yl]-2-fluorophenyl}-2,6-difluorobenzenesulfonamide (204 mg, 0.393 mmol) and stir the solution at room temperature for 3 h to obtain a white precipitate, filter the slurry and wash it with ethyl ether to obtain N-[3-[5-(2-amino-4-pyrimidinyl)-2-(1,1-dimethylethyl)-1,3-thiazo-4-yl]-2-fluorophenyl]-2,6-difluorobenzenesulfonamide methanesulfonate, which is a white crystals (221 mg, 87% yield). $^1$HNMR (400 MHz, DMSO-d6) δ ppm 10.85 (s, 1H) 7.92-8.05 (m, 1H), 7.56-7.72 (m, 1H), 6.91-7.50 (m, 7H), 5.83-5.98 (m, 1H), 2.18-2.32 (m, 3H), 1.36 (s, 9H).

Figure 10:
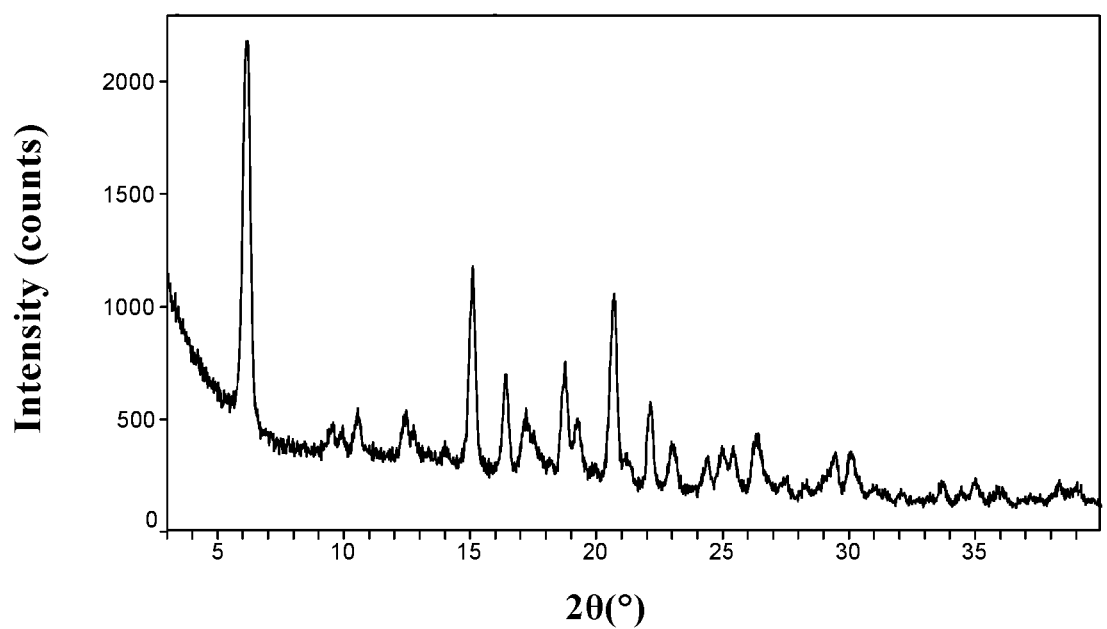
FIG. 10 is the X-ray powder diffraction pattern of the Known Crystal Form I prepared by the method described in example 58a and 58d of patent documents WO2009/137391 or CN200980126781.6.

The X-ray powder diffraction pattern of the obtained crystals as shown in FIG. 10 is consistent with that mentioned in the patent documents WO2009/137391 or CN200980126781.6.

Figure 11:
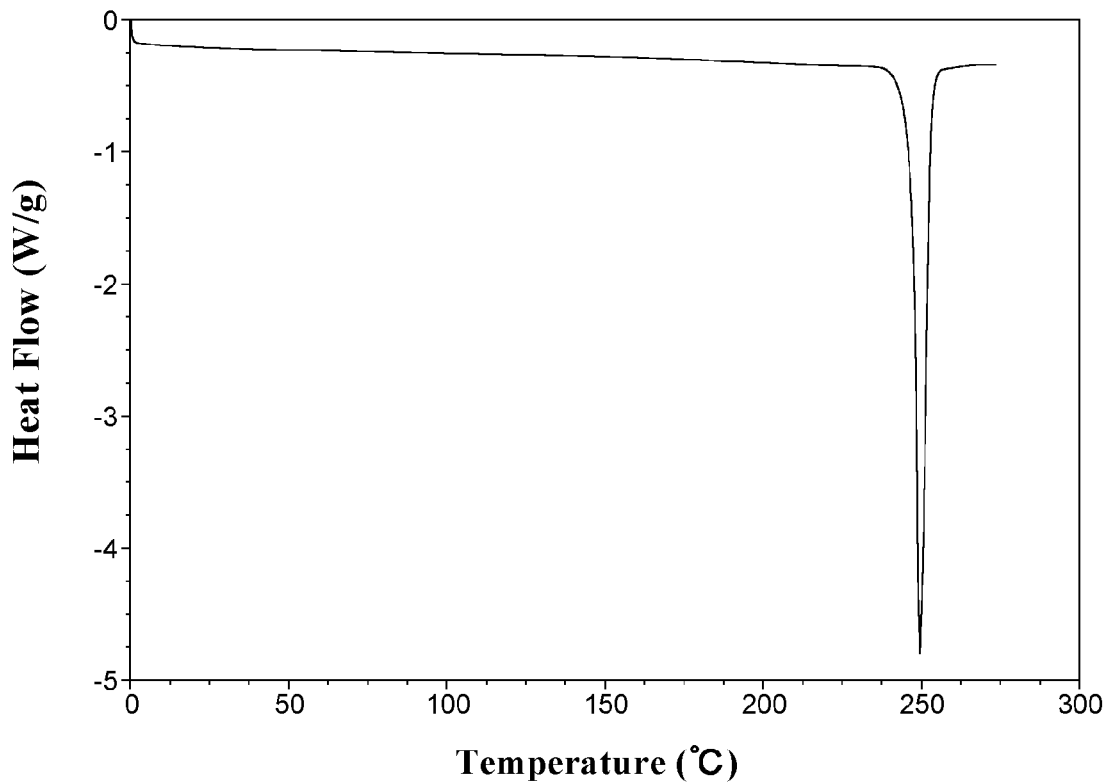
FIG. 11 is the DSC thermogram of the Known Crystal Form I prepared by the method described in example 58a and 58d of patent documents WO2009/137391 or CN200980126781.6.

The DSC thermogram is shown in FIG. 11: the melting range of the Known Crystal Form I is 247° C.~250° C.

Figure 12:
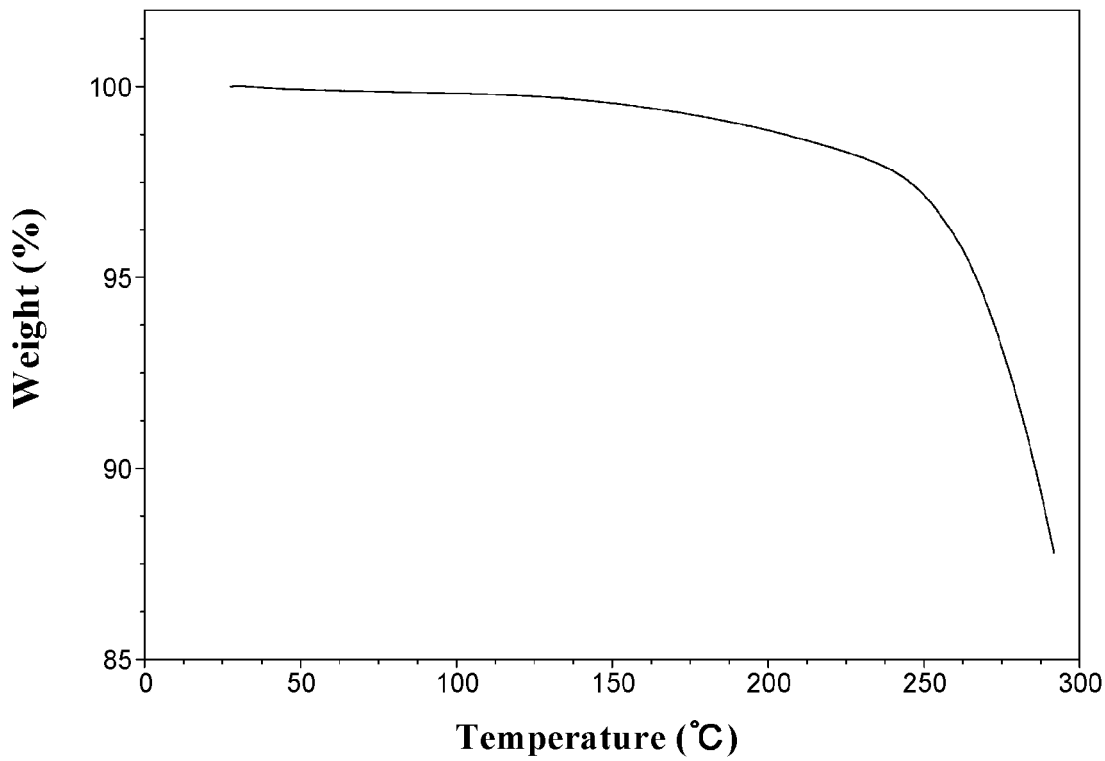
FIG. 12 is the TGA thermogram of the Known Crystal Form I prepared by the method described in example 58a and 58d of patent documents WO2009/137391 or CN200980126781.6.

The TGA thermogram is shown in FIG. 12: the decomposition temperature is 261° C.

Example 1

Place 10.02 mg of Crystal Form IV (prepared via Example 7) in a 5 mL vial, add 0.5 mL water, sonicate it to get a suspension, stir it for 15 minutes at room temperature, centrifuge the suspension, and then separate the solids without drying to get Crystal Form II described by the present invention. The product is 10.00 mg and the yield is 99%.

Figure 6:
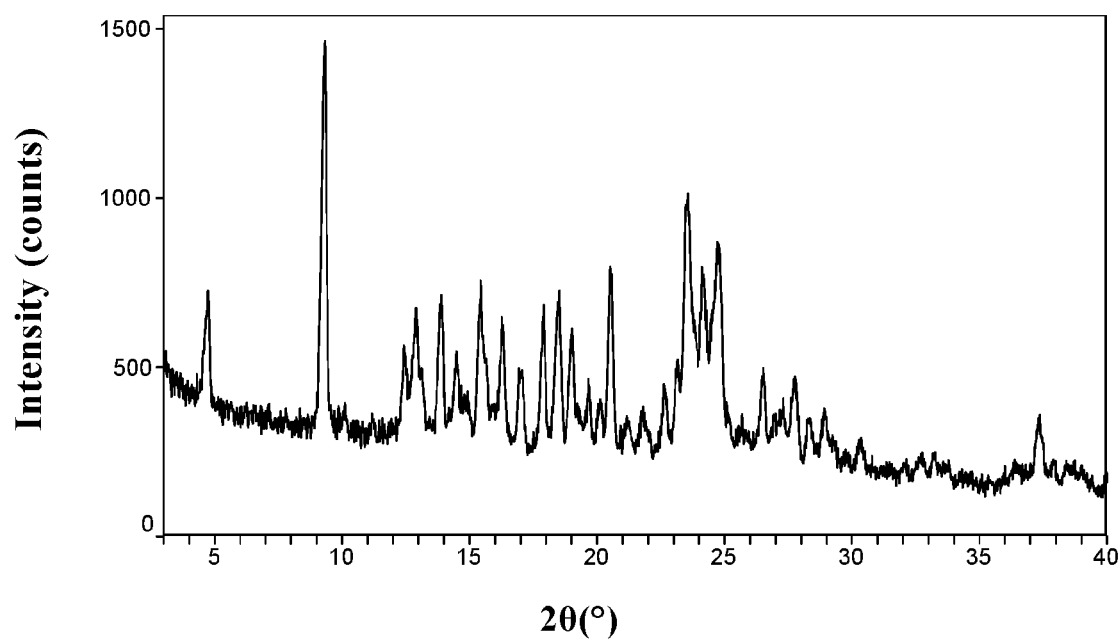
FIG. 6 is X-ray powder diffraction pattern of Crystal Form II of the present invention.

The X-ray powder diffraction pattern is shown in FIG. 6.

Figure 7:
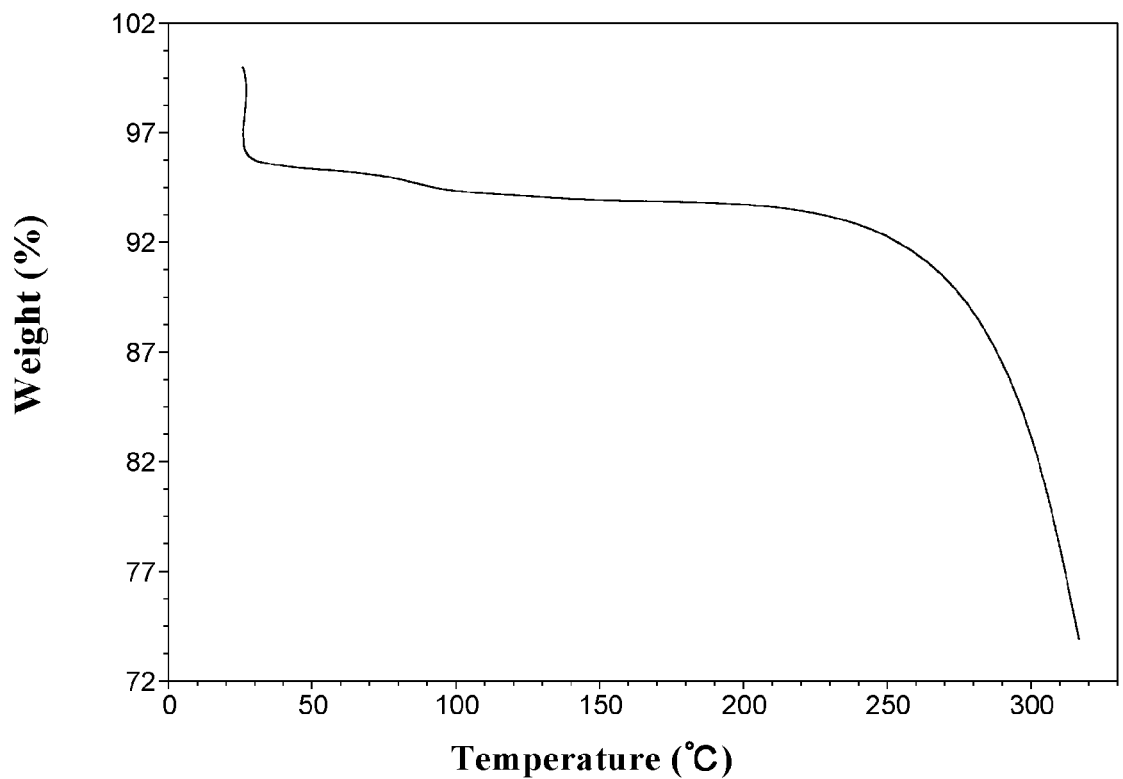
FIG. 7 is the TGA thermogram of Crystal Form II of the present invention.

The TGA thermogram is shown in FIG. 7: the weight loss of Crystal Form II prior to 50° C. is about 4.6% (approximately 1.5 water molecules), the weight loss of Crystal Form II from 50° C.~155° C. is about 1.4% (approximately 0.5 water molecule), the decomposition temperature is 287° C.

Example 2

Place 4.58 mg of the Known Crystal Form I in a 5 mL vial, add 1 mL methanol and 2 mL butanone (the amount of the Known Crystal Form I is 0.1 times of its solubility in the mixed solvent at room temperature), sonicate it for 5 min to get a clear solution, then filter it with 0.45 µm organic filter membrane, place the filtrate in an uncovered 5 mL vial and evaporate it to recrystallize under nitrogen blowing, after 10 min, centrifuge to separate the solids, without drying, get Crystal Form III described by the present invention. The product is 4.02 mg and the yield is 88%.

Figure 8:
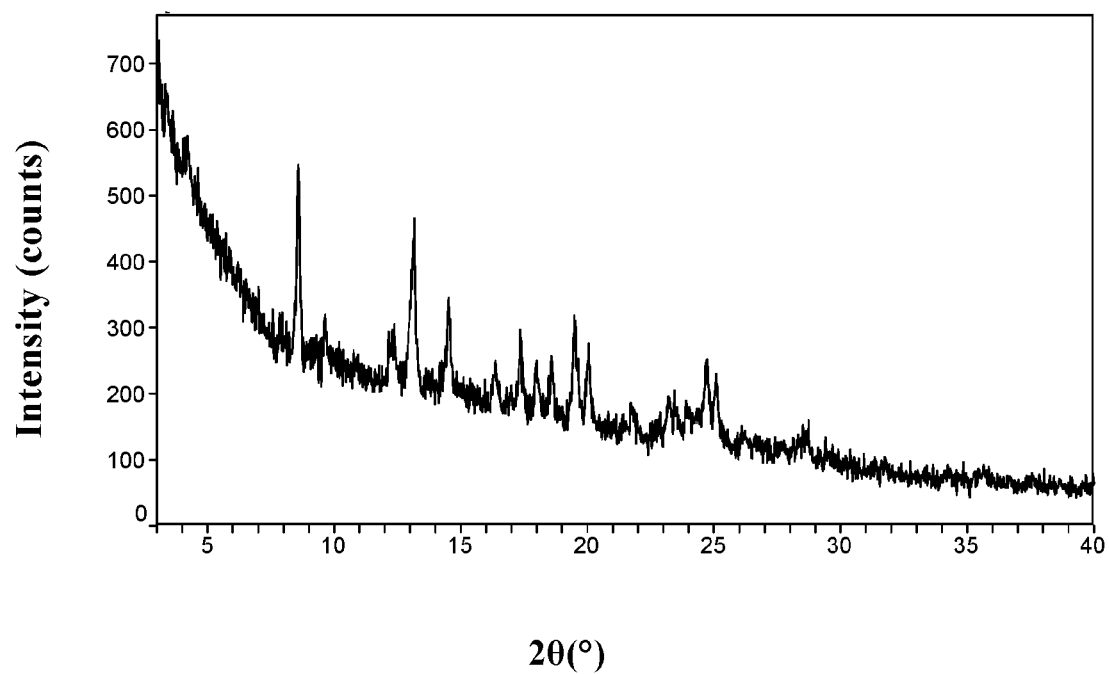
FIG. 8 is the X-ray powder diffraction pattern of Crystal Form III of the present invention.

The X-ray powder diffraction pattern is as shown in FIG. 8.

Example 3

Place 5.98 mg of the Known Crystal Form I in a 20 mL vial, add 5 mL methanol and 0.05 mL ethyl acetate (the amount of the Known Crystal Form I is 1 time of its solubility in the mixed solvent at room temperature), sonicate for 5 min to get a clear solution, then filter it with 0.45 µm organic filter membrane, place the filtrate in an uncovered 20 mL vial and evaporate to recrystallize under nitrogen blowing at 40° C., after 60 min, separate the solids by centrifugation, without drying, get Crystal Form III described by the present invention. The solids are 3.22 mg and the yield is 54%. The X-ray powder diffraction pattern is substantially consistent with that of FIG. 8.

Example 4

Place 5.54 mg of the Known Crystal Form I in a 5 mL vial, add 1.5 mL methanol and 0.3 mL ethyl ether (the amount of the Known Crystal Form I is 0.8 times of its solubility in the mixed solvent at room temperature), sonicate for 5 min to get a clear solution, then filter it with 0.45 µm organic filter membrane, place the filtrate in an uncovered 5 mL vial and evaporate to recrystallize under nitrogen blowing, after 1 min, separate the solids by centrifugation, without drying, get Crystal Form III described by the present invention. The resulting solids are 4.85 mg and the yield is 87%. The X-ray powder diffraction pattern is substantially consistent with that of FIG. 8.

Example 5

Place 3.31 mg of the Known Crystal Form I in a 5 mL vial, add 0.3 mL methanol and 3 mL sec-butyl alcohol (the amount of the Known Crystal Form I is 0.5 times of its solubility in the mixed solvent at room temperature), sonicate for 5 min to get a clear solution, then filter it with 0.45 µm organic filter membrane, place the filtrate in an uncovered 5 mL vial and evaporate to recrystallize under nitrogen blowing, after 10 min, separate the solids by centrifugation, without drying, get Crystal Form III described the present invention. The product is 2.05 mg and the yield is 62%. The X-ray powder diffraction pattern is substantially consistent with that of FIG. 8.

Example 6

Place 3.31 mg of the Known Crystal Form I in a 5 mL vial, add 0.5 mL methanol and 1 mL n-butanol (the amount of the Known Crystal Form I is 0.8 times of its solubility in the mixed solvent at room temperature), sonicate for 5 min to get a clear solution, then filter it with 0.45 µm organic filter membrane, place the filtrate in an uncovered 5 mL vial and evaporate to recrystallize under nitrogen blowing, after 10 min, separate the solids by centrifugation, without drying, get Crystal Form III described by the present invention. The product is 3.00 mg and the yield is 91%. The X-ray powder diffraction pattern is substantially consistent with that of FIG. 8.

Example 7

Place 44.20 mg of the Known Crystal Form I in a 20 mL vial, add 2 mL methanol and 5 mL tetrahydrofuran (the amount of the Known Crystal Form I is 1 time of its solubility in the mixed solvent at room temperature), sonicate for 5 min to get a clear solution, then filter it with 0.45 µm organic filter membrane, place the filtrate in an uncovered 20 mL vial and evaporate to recrystallize at room temperature, separate the solids by centrifugation, vacuum drying for 16 hours at 40° C., get Crystal Form IV of the present invention. The product is 43.0 mg and the yield is 97%.

The X-ray powder diffraction pattern is shown in FIG. 1.

Figure 2:
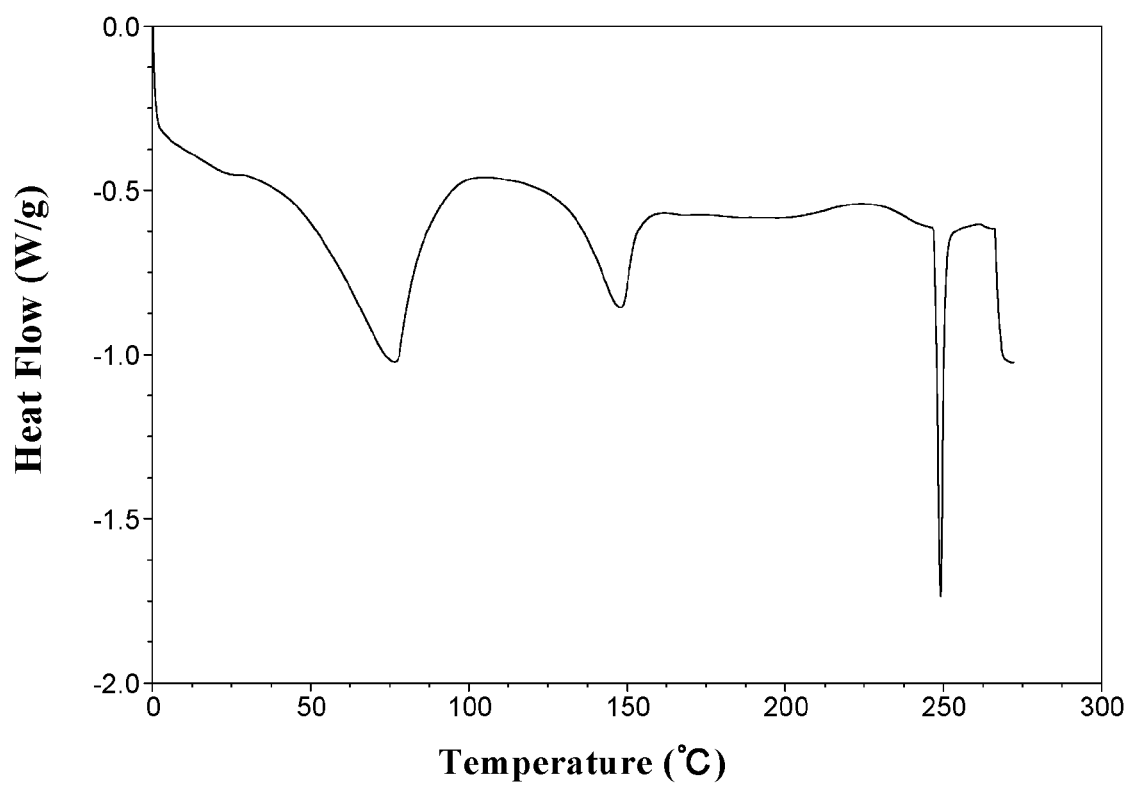
FIG. 2 is the DSC thermogram of Crystal Form IV of the present invention.

The DSC thermogram is shown in FIG. 2: the Crystal Form IV has a broad and large endothermic peak (the solvent peak) at 15° C.~105° C., the melting range of the dehydrated sample is 132° C.~148° C., followed by an exothermic form transformation peak at 200° C.~245° C. and a melting point at 249° C.

Figure 3:
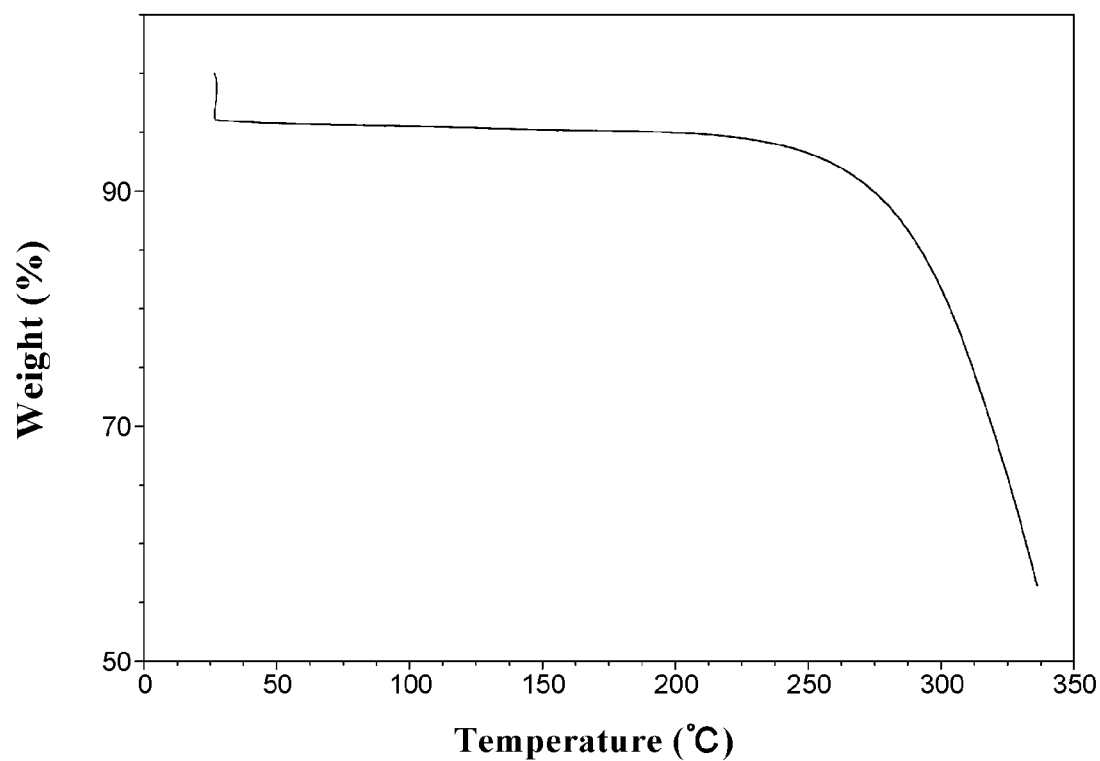
FIG. 3 is the TGA thermogram of Crystal Form IV of the present invention.

The TGA thermogram is shown in FIG. 3: the weight loss of Crystal Form IV prior to 65° C. is about 4.3% (approximately 1.5 water molecules), and the decomposition temperature is 291° C.

Figure 4:
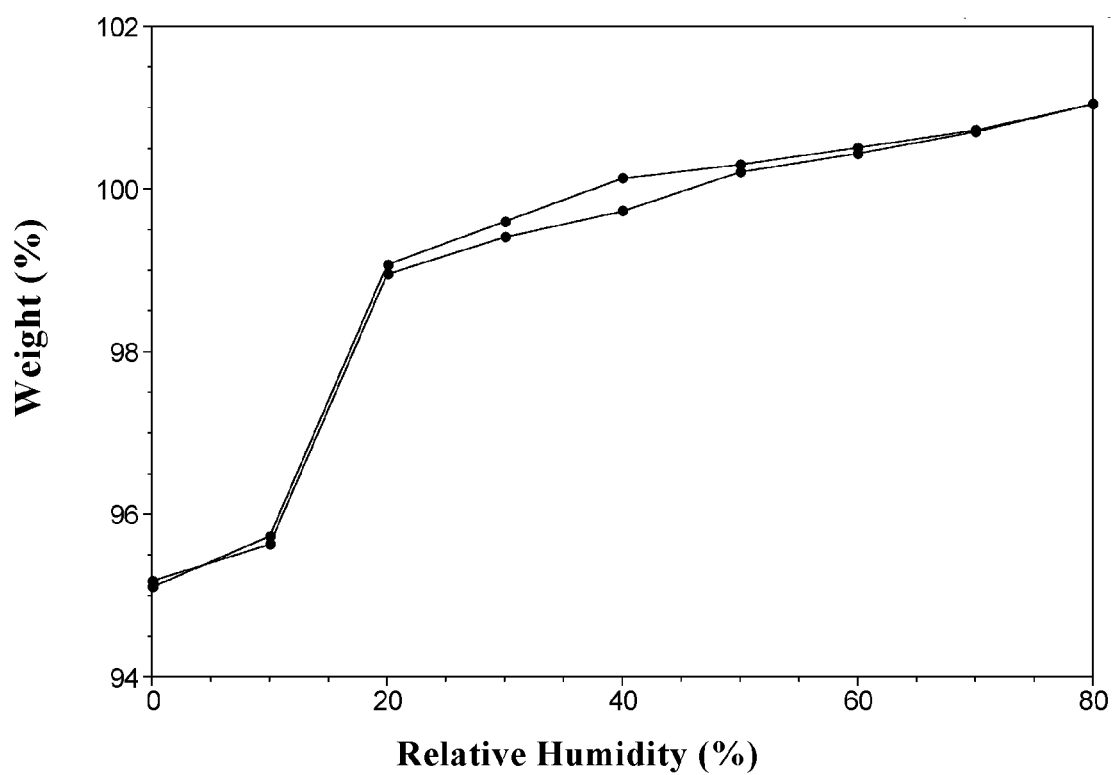
FIG. 4 is the dynamic vapor sorption isothermal plot of Crystal Form IV of the present invention.

The dynamic vapor sorption isothermal plot is shown in FIG. 4, showing a weight change of 2.0% between 20% RH-80% RH.

Figure 5:
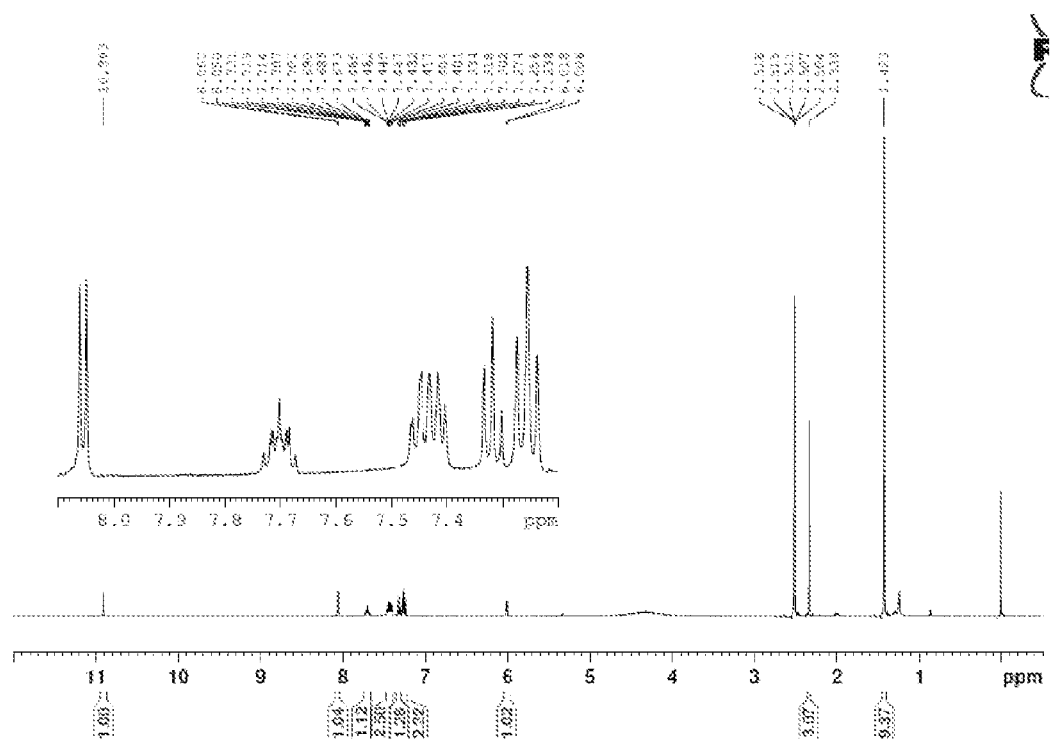
FIG. 5 is the $^1$HNMR spectrum of Crystal Form IV of the present invention.

The $^1$HNMR is shown in FIG. 5, indicating a methanesulfonate salt.

Example 8

Place 22.22 mg of the Known Crystal Form I in a 20 mL vial, add 15 mL acetone (the amount of the Known Crystal Form I is 0.8 times of its solubility in acetone at room temperature), sonicate for 5 min to get a clear solution, then filter it with 0.45 µm organic filter membrane, place the filtrate in an uncovered 20 mL vial and evaporate to recrystallize at room temperature, separate the solids by centrifugation, vacuum drying the solids for 16 hours at 40° C., get Crystal Form IV described by the present invention. The product is 20.18 mg and the yield is 91%. The X-ray powder diffraction pattern is substantially consistent with that of FIG. 1.

Example 9

Place 9.58 of mg the Known Crystal Form I in a 20 mL vial, add 15 mL isopropanol (the amount of the Known Crystal Form I is 0.5 times of its solubility in isopropanol at room temperature), sonicate for 5 min to get a clear solution, then filter it with 0.45 μm organic filter membrane, place the filtrate in an uncovered 20 mL vial and add 0.35 mg of polyacrylic acid (the molecular weight is about 5000), evaporate to recrystallize at room temperature, separate the solids by centrifugation, vacuum drying the solids for 16 hours at 40° C., get Crystal Form IV described by the present invention. The product is 8.95 mg and the yield is 93%. The X-ray powder diffraction pattern is substantially consistent with that of FIG. 1.

Example 10

Place 5.02 mg of the Crystal Form II in a 5 mL vial, vacuum drying the solids for 16 hours at 40° C., and get Crystal Form IV described by the present invention. The product is 4.90 mg and the yield is 98%. The X-ray powder diffraction pattern is substantially consistent with that of FIG. 1.

Example 11

Take 4.20 mg of Crystal Form II and run it in TGA, using the following procedure: "high-resolution sensitivity 3.00, resolution 5.00, heating to 120° C. at a rate of 10.00° C./min"; after the procedure, let it cool naturally to room temperature; then, place the sample in air for 1 h to obtain Crystal Form IV described by the present invention. The product is 4.05 mg and the yield is 96%. The X-ray powder diffraction pattern is substantially consistent with that of FIG. 1.

Example 12

Take 5.00 mg of the Crystal Form V (prepared by Example 13) and let it sit uncovered at room temperature for 30 min, and get Crystal Form IV described by the present invention. The product is 5.00 mg and the yield is 100%. The X-ray powder diffraction pattern is substantially consistent with that of FIG. 1.

Example 13

Figure 9:
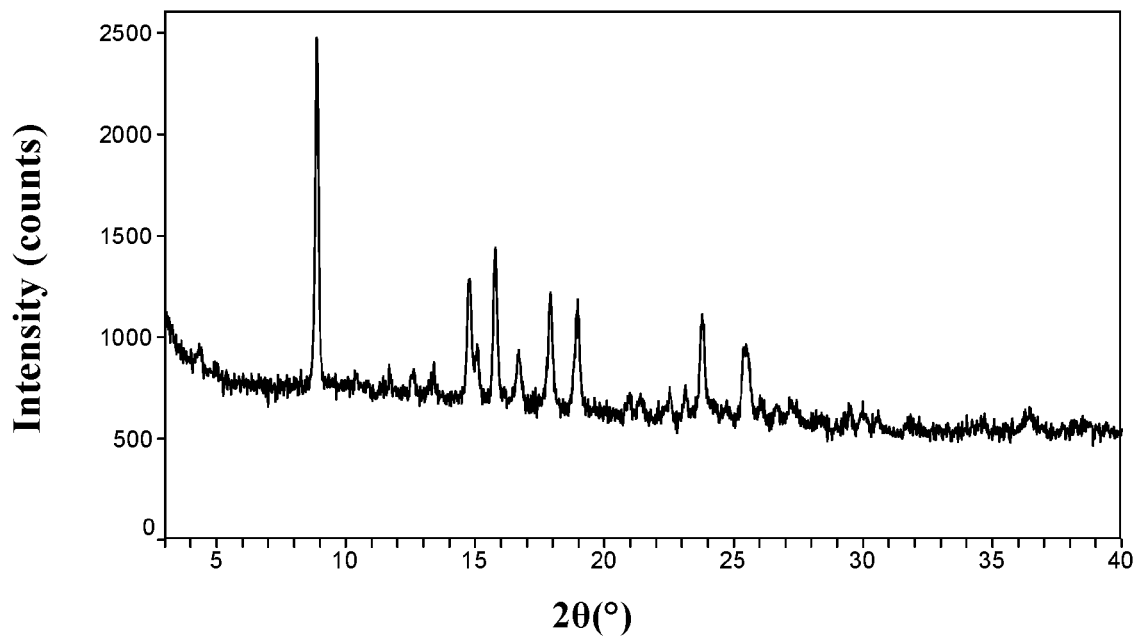
FIG. 9 is the X-ray powder diffraction pattern of Crystal Form V of the present invention.

Place 8.52 mg of the Crystal Form IV in a copper pan preheated to 60° C., kept it at 60° C. for 1 hour, and get Crystal Form V described by the present invention. The product is 8.07 mg and the yield is 95%. The X-ray powder diffraction pattern is as shown in FIG. 9.

Example 14

Preparation of Capsules Containing the Crystal Forms of the Present Invention

Components in each capsule: 71 mg Active Pharmaceutical Ingredient (API, selected from the group consisting of the crystal forms of Dabrafenib methanesulfonate of the present invention, including Crystal Form II, Crystal Form III, Crystal Form IV and Crystal Form V)+60 mg microcrystalline cellulose (Avicel)+13 mg sodium carboxymethyl starch (SSG).

Each size 0# hard capsule contains 144 mg of powders. The weight of Avicel/SSG may be reasonably approximate.

Steps

1) Appropriately/according to the actual need, separate thard capsules into halves and mark/identify each half.

2) Place the bottom halves of the capsules in capsule filling machine, with the filling funnel on the top.

3) Weigh each component (Avicel, SSG, API) on thin weighing paper (between each weighing, be sure to coat tar on the analytical balance).

4) Record the weight of each component.

5) Carefully and thoroughly mix the dry powders on the thin weighing paper with a small spatula.

6) Through the funnel, carefully transfer the mixed powders to the capsules.

7) Place the top halves of the capsules on the capsules, close tightly, then shake the capsules to blend/disperse the components.

8) If the powders are filled near the top of the capsules, slightly tap the capsule by hand to settle down the powders.

9) Place such capsules in a small appropriately marked bottle (which should be large enough to remove the capsules easily).

Example 15

Preparation of Tablets Containing the Crystal Forms of the Present Invention

| Component | Content (mg/tablet) | % w/w |
| --- | --- | --- |
| Tablet Core | | |
| API (selected from the group consisting of the Crystal Forms of Dabrafenib methanesulfonate of the present invention) | 479.9 | 74.9 |
| Lactose monohydrate | 59.0 | 9.2 |
| Polysorbate 80 | 1.0 | 0.2 |
| Polyvinylpyrrolidone | 40.0 | 6.2 |
| Colloidal silicon dioxide | 5.5 | 0.9 |
| Cross-linked polyvinylpyrrolidone | 51.0 | 8.0 |
| Magnesium stearate | 4.5 | 0.7 |
| Purified water | qs | |
| Film coating | | |
| Opadry ®Orange, YS-1-13065-A | 17.0 | 3.0 |
| Purified water | qs | |

Note:
"qs" in the above table means that such solvent or water will be removed in the final product.

Steps

1) Sieve lactose monohydrate, colloidal silicon dioxide, cross-linked polyvinylpyrrolidone and half polyvinylpyrrolidone.

2) Add API (selected from the Crystal Forms of Dabrafenib methanesulfonate of the present invention, including Crystal Form II, Crystal Form III, Crystal Form IV and Crystal Form V).

3) Granulate the mixture in a high-shear granulator with granulating solution containing dissolved polysorbate 80 and other half polyvinylpyrrolidone in purified water.

4) Using Comil 197 with a 0.375" screen to grind the granules.

5) Using a fluidized bed dryer to dry the granules.

6) Using Comil 197 with a 0.075" screen to grind the granules.

7) Add cross-linked polyvinylpyrrolidone and magnesium stearate.
8) Mix for 5 min.
9) Compress the solids into tablets.
10) Coat the tablets with an aqueous film coating.

Experimental Example 1

Compare the stability, the hygroscopicity, melting points, decomposition temperatures and dissolution profiles of Crystal Form IV prepared by Example 7 and the Known Crystal Form I. The results are shown in Table 1.

The stability is performed by comparing the storage stability and the stirring test in water on crystalline forms.

The storage stability is performed by placing the samples under a constant condition (i.e. under constant humidity or constant temperature) for a certain period of time, and then comparing their XRPDs before and after placement.

The stirring test in water is performed by, for each crystalline form, adding an equal amount of the sample (10 mg) to an equal amount of water (1 mL) to form a suspension, stirring the suspensions for a certain time at room temperature, and then comparing their XRPDs.

Figure 13:
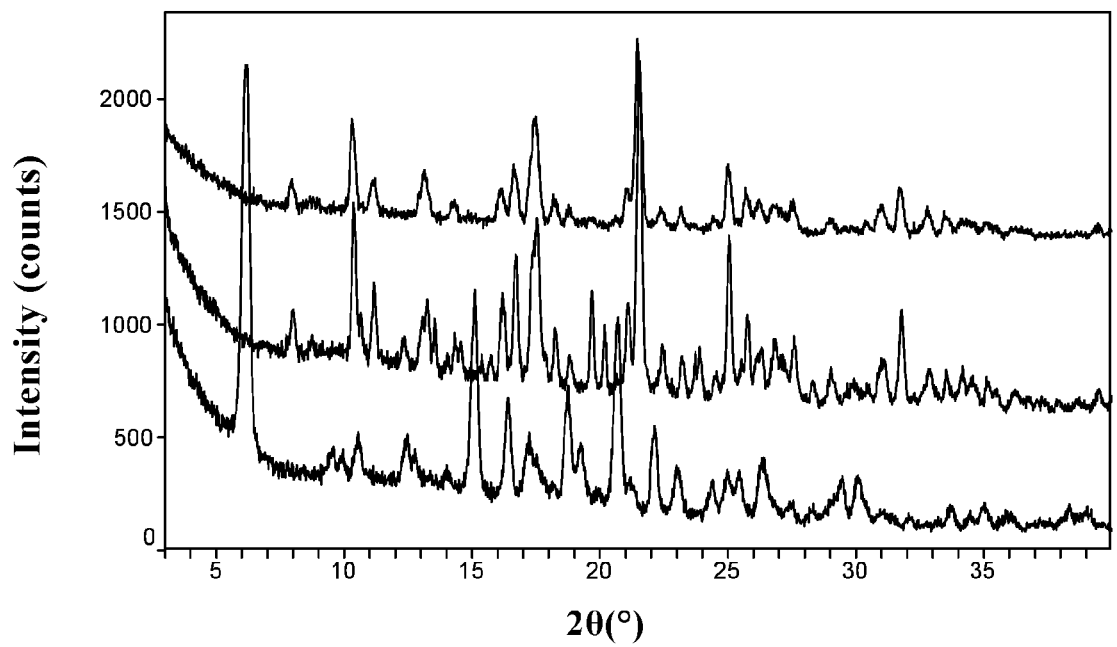
FIG. 13 is the X-ray powder diffraction comparison patterns of the Known Crystal Form I at every stage in Experimental Example 1, wherein, the samples from top to bottom are: Dabrafenib free base hydrate, the sample obtained by stirring the Known Crystal Form I in water for 15 minutes, the Known Crystal Form I.

FIG. 13 is the XRPD comparison patterns of the Known Crystal Form I at every stage in Experimental Example 1, wherein, the samples from top to bottom are: Dabrafenib free base hydrate, the sample obtained from stirring the Known Crystal Form I in water for 15 min (this XRPD pattern shows this sample's crystalline form is consistent with the above-mentioned Dabrafenib free base hydrate), and the Known Crystal Form I.

Figure 14:
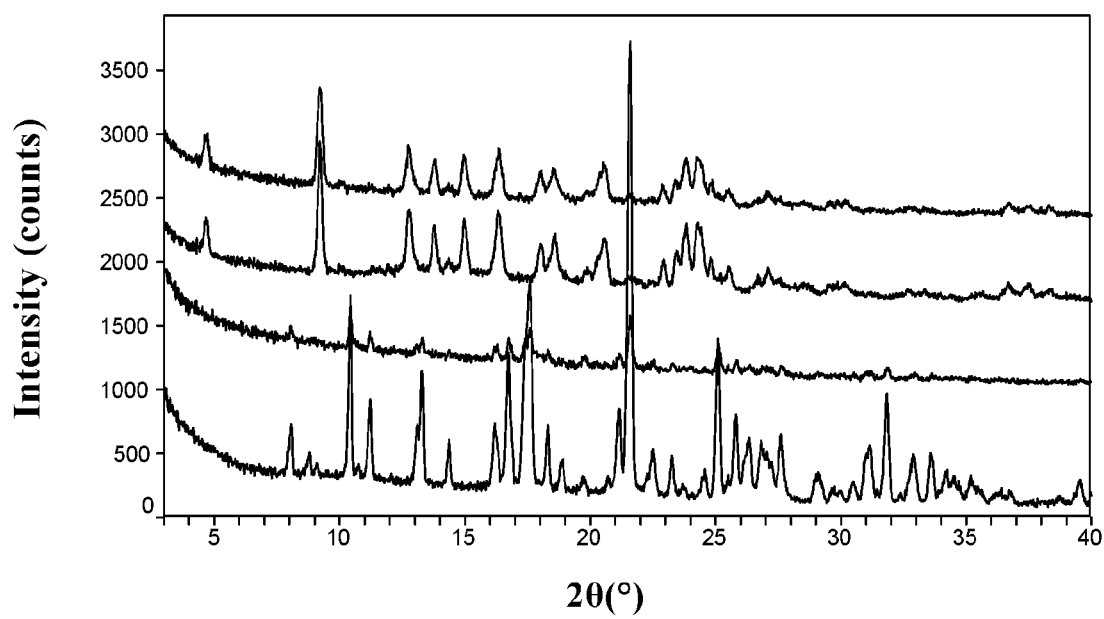
FIG. 14 is the X-ray powder diffraction comparison patterns of the Crystal Form IV of the present invention at every stage in Experimental Example 1, wherein, the samples from top to bottom are: the Crystal Form IV, the sample obtained by stirring the Crystal Form IV in water for 15 minutes, the sample obtained by stirring the Crystal Form IV in water overnight, Dabrafenib free base hydrate.

FIG. 14 is the XRPD comparison patterns of Crystal Form IV of the present invention at every stage in Experimental Example 1, wherein, the samples from top to bottom are: the Crystal Form IV, the sample obtained from stirring the Crystal Form IV in water for 15 min (this XRPD pattern shows this sample's crystalline form is consistent with the above-mentioned Crystal Form IV, indicating it remains Crystal Form IV), the sample obtained from stirring the Crystal Form IV in water overnight, and Dabrafenib free base hydrate.

Compare melting points obtained by DSC tests.

Compare decomposition temperatures obtained by TGA tests.

Compare hygroscopicity in weight changes of samples between 20%-80% RH obtained by DVS tests.

Figure 15:
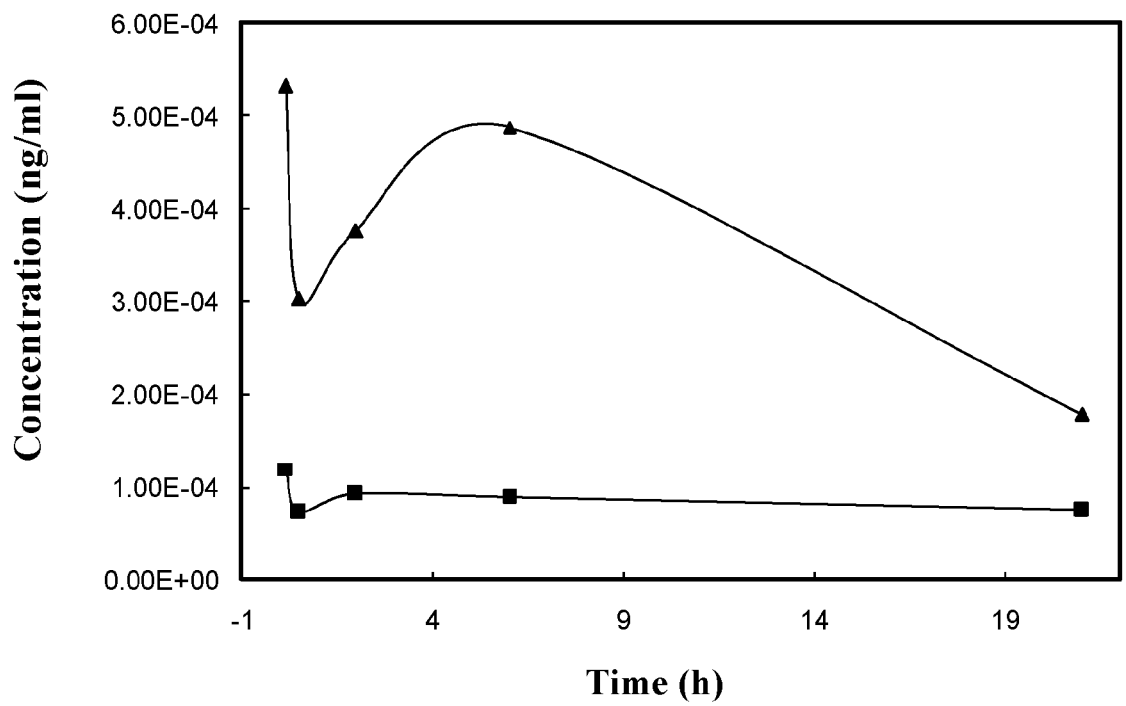
FIG. 15 is the comparison of dissolution profiles between Crystal Form IV and the Known Crystal Form I in Experimental Example 1 (▲ refers to Crystal Form IV, ■ refers to the Known Crystal Form I).

The comparison of dissolution profiles is performed by the following procedures: place about 6 mg the sample in a 20 mg vial, add 15 mL ultrapure water, and then seal the vial. A suspension is obtained from sonication with a working power of 40 Khz at room temperature, then take 1 mL of the suspension at 10 min, 30 min, 2 hr and 6 hr, respectively; filter it with 0.45 μm organic filter membrane to, take the filtrate to be measured by HPLC; stir the remaining suspension for 16 hr at room temperature, and then filter it with 0.45 μm organic filter membrane, take the filtrate to be measured by HPLC. FIG. 15 is the comparison plot of dissolution profiles of Crystal Form IV and the Known Crystal Form I in Experimental Example 1 (▲ refers to Crystal Form IV, ■ refers to the Known Crystal Form I).

TABLE 1

Property Comparison Results of Different Crystal Forms

| | Items | The Known Crystal Form I | Crystal Form IV of the present invention |
|---|---|---|---|
| Stability | Storage at room temperature | After stored for 1 month at room temperature and at room temperature - 97% RH, respectively, the crystal forms remained unchanged. | |
| | Stirring test in water | After stirred in water for 15 min, it converted to the free base (FIG. 13) | After stirred in water for 15 min, it remained as methanesulfonate and after stirred overnight, it converted to the free base (FIG. 14). |
| Melting point | | The melting range is 247~250° C. (FIG. 11) | There is a broad and large endothermic peak (the dehydration peak) at 15° C.~105° C., a melting range of the dehydrated sample between 132 to 148° C., an exothermic form conversion peak at 200° C.~245° C., and a melting point at 247~249° C. (FIG. 2) |
| Decomposition temperature | | 261° C. (FIG. 12) | 291° C. (FIG. 3) |
| Hygroscopicity | | Non-hygroscopic; the form is stable at 25° C. and 20-80% RH. | The form is table at 25° C. and 20-80% RH; the sample may dehydrate to form an anhydrate below 20% RH (e.g. under a drying $N_2$ flow) (FIG. 3). |
| Dissolution (FIG. 15) | 10 minutes | $1.20 \times 10^{-4}$ mg/mL | $5.32 \times 10^{-4}$ mg/mL |
| | 30 minutes | $7.23 \times 10^{-5}$ mg/mL | $3.03 \times 10^{-4}$ mg/mL |
| | 2 hours | $9.28 \times 10^{-5}$ mg/mL | $3.76 \times 10^{-4}$ mg/mL |
| | 6 hours | $8.88 \times 10^{-5}$ mg/mL | $4.88 \times 10^{-4}$ mg/mL |
| | 6 hours + 16 hours | $7.48 \times 10^{-5}$ mg/mL | $1.78 \times 10^{-4}$ mg/mL |
| | Summary | 1) Comparing the dissolution profiles from 0~22 h, the dissolution rate of Crystal Form IV is higher than that of the Known Crystal Form I at any test point; 2) The time to the end point in water during dissolution for Crystal Form IV is shorter than that of the Known Crystal Form I. | |

The results are as shown in Table 1 and the conclusions are:

1) When stored for one month at room temperature or at room temperature–97% RH, respectively, Crystal Form IV and the Known Crystal Form I remained unchanged.

2) The Known Crystal Form I converted to its free base after stirred for 15 minutes in the water suspension (converted to the free base monohydrate confirmed by TGA and its XRPD is consistent with that of the patent application PCT/CN2014/074883); while Crystal Form IV still remained as methanesulfonate after stirred for 15 minutes in the water suspension (the ¹HNMR spectrum is consistent with FIG. 5; its XRPD pattern is consistent with that of the above-mentioned Crystal Form IV, indicating it remained Crystal Form IV); Crystal Form IV converted to its free base after stirred overnight (confirmed by TGA as the free base monohydrate and its XRPD is consistent with that of the patent application PCT/CN2014/074883). These indicate that Crystal Form IV is better in maintaining in the state of methanesulfonate that has higher than that of free base, and Crystal Form IV has better stability in water or aqueous system.

3) Comparing the dissolution profiles from 0~22 h, the dissolution rate of Crystal Form IV is higher than that of the Known Crystal Form I at any test point. This indicates that Crystal Form IV has better dissolution rate and bioavailabilty.

Experimental Example 2

The stability of the Known Crystal Form I of Dabrafenib methanesulfonate and Crystal Form IV of the present invention during wet granulation in formulation process was studied.
The formulation is:

| Component | Content (mg/tablet) |
|---|---|
| API (the Known Crystal Form I or Crystal Form IV of the present invention) | 118.5 |
| Lactose (monohydrate) | 280 |
| Microcrystalline cellulose | 112 |
| Polyethylene glycol 6000 | 8 |

Wet granulation experiments in the formulation process were parallel experiments. The specific steps are:
1) Blend API (the Known Crystal Form I or Crystal Form IV of the present invention), lactose (monohydrate) and microcrystalline cellulose uniformly.
2) Make the above mixture into soft materials by using appropriate amount of 50% aqueous ethanol solution, screen to produce wet granules.
3) Dry the wet granules and then granulate them, blend with polyethylene glycol 6000 uniformly and then compress them into tablets.

Characterize the Known Crystal Form I and Crystal Form IV of the present invention samples obtained from the formulation process of: (1) the sample obtained from physically mixing lactose monohydrate and microcrystalline cellulose at the ratios per the formulation; (2) the sample obtained from physically mixing of API, lactose monohydrate and microcrystalline cellulose at the ratios per the formulation; (3) the wet granule sample obtained from the wet granulation process (excluding the compressed tablets in Step 3). See XRPDs in FIG. 16 and FIG. 17.

Figure 16:
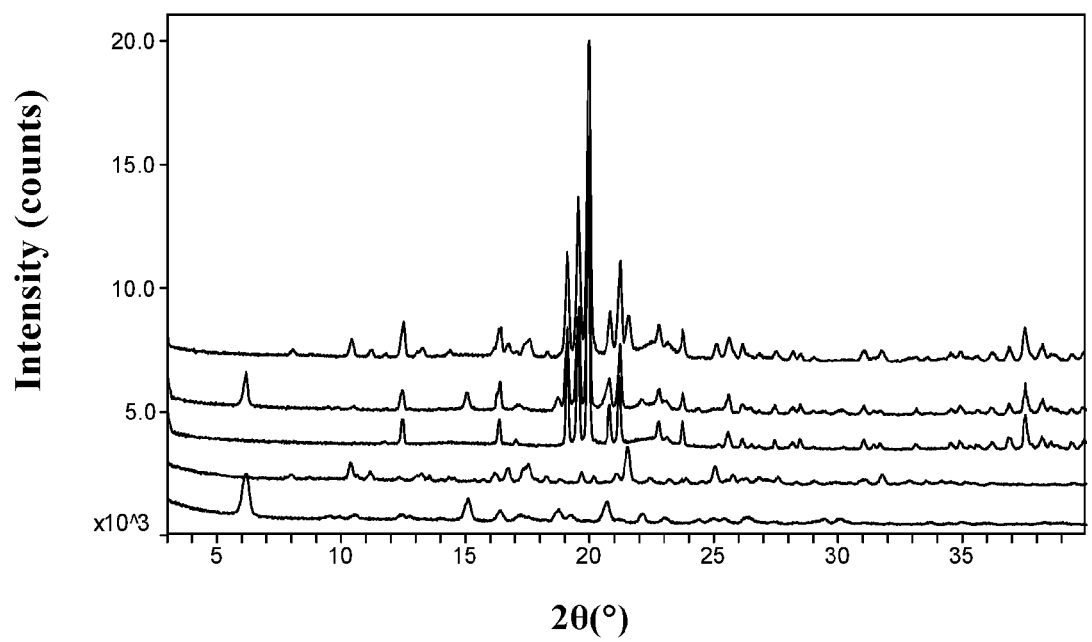
FIG. 16 is the X-ray powder diffraction comparison patterns of the Known Crystal Form I at every stage in Experimental Example 2, wherein, the samples from top to bottom are: the sample obtained from wet granulation (not including the Step 3 of compressing tablets) of the Known Crystal Form I as API, the sample obtained from physically mixing the Known Crystal Form I and the excipients at ratios per the formulation, the sample obtained from physically mixing lactose monohydrate and microcrystalline cellulose at ratios per the formulation, Dabrafenib free base hydrate, and the Known Crystal Form I.

According to FIG. 16 and FIG. 17:
1) With respect to the Known Crystal Form I, compared with the XRPD of the sample (2) obtained from physically mixing API, lactose monohydrate and microcrystalline cellulose at ratios per the formulation, the XRPD of the wet granule sample (3) obtained from the wet granulation process (excluding the compressed tablets in Step 3) shows that the API has partially or totally converted to Dabrafenib free base hydrate (confirmed by TGA as free base monohydrate and its XRPD is consistent with that of the patent application PCT/CN2014/074883). These indicate that the Known Crystal Form I is unstable in the wet granulation process.

2) With respect to Crystal Form IV, compared with the XRPD of the sample (2) obtained from physically mixing API, lactose monohydrate and microcrystalline cellulose at ratios per the formulation, the XRPD of the wet granule sample (3) obtained from the wet granulation process (excluding the compressed tablets in Step 3) shows that the API still kept as Dabrafenib methanesulfonate (the ¹HNMR spectrum is consistent with FIG. 5; the XRPD pattern shows that it is consistent with that of the above-mentioned Crystal Form IV, indicating that it remained as Crystal Form IV). These indicate that Crystal Form IV is stable in the wet granulation process.

The above experiments show that, Crystal Form IV of the present invention is more stable in the wet granulation process and is easier to granulate; therefore, it is an advantageous crystal form.

In addition, after the tablets of Crystal Form IV were stored for 1 month at 25° C./60% RH, its crystal form still is stable.

Experimental Example 3

Compare the capsule dissolution rate of Crystal Form IV prepared by Example 7 with that of the Known Crystal Form I. The capsule formulation is:

| Component | Content (mg/capsule) |
|---|---|
| API (the Known Crystal Form I or Crystal Form IV of the present invention) | 100 |
| Mannitol | 55 |
| Talc | 16 |
| Magnesium stearate | 4 |

The dissolution rate was performed by reference of Chinese Pharmacopoeia 2010, using the paddle method. Use 500 mL 0.1% lauryl sodium sulfate aqueous solution as the dissolution medium, keep the temperature at 37° C. and the stirring speed at 50 rpm; withdraw a 3 mL specimen at each of the times: 2 min, 5 min, 10 min, 30 min, 60 min and 120 min; replace the aliquots withdrawn for analysis with equal volumes of 0.1% lauryl sodium sulfate aqueous solution. Perform HPLC analysis on samples from each time interval for concentration information. See results in Table 2.

TABLE 2

Comparison of dissolution rate of different crystal forms from capsules

| Sampling time | Dissolution rate of the Known Crystal Form I capsules | Dissolution rate of Crystal Form IV capsules |
|---|---|---|
| 2 min | 8.01% | 17.0% |
| 5 min | 16.3% | 24.0% |
| 10 min | 23.0% | 33.0% |
| 30 min | 32.3% | 59.7% |
| 60 min | 75.0% | 99.3% |
| 120 min | 101.3% | 150.7% |

From the results in Table 2, it is concluded that comparing the dissolution quantity of 0~120 min, the dissolution quantity of Crystal Form IV capsule is larger than that of the Known Crystal Form I capsule at any test point. This indicates that Crystal Form IV capsule has better dissolution rate and bioavailabilty.

All patent documents and non-patent publications referred to herein are incorporated by reference entirely into the present application.

In the present application, the above general description of the invention and the description of specific embodiments shall not be considered as the restriction on the technical scheme of such invention. The technicians in this field, according to the disclosure of the present application and under the precondition of not violating the elements constituting the related invention, may add, reduce or combine the technical features disclosed in the above general description or/and specific embodiments, so as to form other technical schemes within the present invention.

What is claimed is:

1. A Crystal Form II of Dabrafenib methanesulfonate with the structural formula shown below, and Crystal Form II is a hydrate,

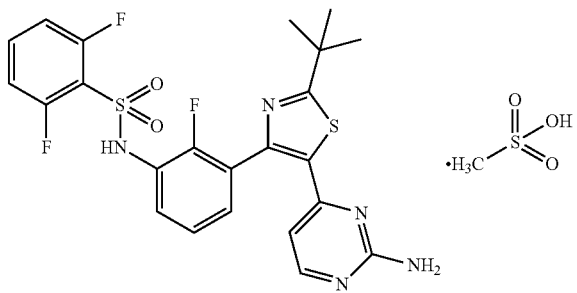

wherein the Crystal Form II of Dabrafenib methanesulfonate is characterized by a X-ray powder diffraction pattern measured using Cu-Kα radiation having the characteristic peaks at the diffraction angles 2θ of 4.7±0.2°, 9.3±0.2°, 13.9±0.2°, 15.4±0.2°, 17.0±0.2° and 19.0±0.2°.

2. The Crystal Form II of Dabrafenib methanesulfonate according to claim 1, wherein the Crystal Form II of Dabrafenib methanesulfonate is characterized by a X-ray powder diffraction pattern having the characteristic peaks at the diffraction angles 2θ of 4.7±0.2°, 9.3±0.2°, 12.9±0.2°, 13.9±0.2°, 15.4±0.2°, 17.0±0.2°, 17.9±0.2°, 18.5±0.2°, 19.0±0.2°, 20.5±0.2°, 23.6±0.2° and 24.8±0.2°.

3. The Crystal Form II of Dabrafenib methanesulfonate according to claim 2, wherein the Crystal Form II of Dabrafenib methanesulfonate is characterized by a X-ray powder diffraction pattern having the following characteristic peaks at the diffraction angles 2θ and their relative intensities:

| Diffraction angle 2θ | Relative intensity % |
|---|---|
| 4.7 ± 0.2° | 29.2 |
| 9.3 ± 0.2° | 100.0 |
| 12.4 ± 0.2° | 20.9 |
| 12.9 ± 0.2° | 30.1 |
| 13.9 ± 0.2° | 32.1 |
| 14.5 ± 0.2° | 19.0 |
| 15.4 ± 0.2° | 35.3 |
| 16.3 ± 0.2° | 26.5 |
| 17.0 ± 0.2° | 18.9 |
| 17.9 ± 0.2° | 34.8 |
| 18.5 ± 0.2° | 36.8 |
| 19.0 ± 0.2° | 27.0 |
| 19.7 ± 0.2° | 14.9 |
| 20.5 ± 0.2° | 45.3 |
| 22.6 ± 0.2° | 14.9 |
| 23.6 ± 0.2° | 49.1 |
| 24.1 ± 0.2° | 33.3 |
| 24.8 ± 0.2° | 40.9 |
| 26.5 ± 0.2° | 18.7 |
| 27.3 ± 0.2° | 12.5 |
| 27.8 ± 0.2° | 19.6 |
| 28.9 ± 0.2° | 13.5 |
| 37.4 ± 0.2° | 15.6. |

4. A method of preparing the Crystal Form II of Dabrafenib methanesulfonate according to claim 1, comprising:
suspending Crystal Form IV of Dabrafenib methanesulfonate in water to form a suspension, stirring to recrystallize, and then separating the precipitated crystals without drying to get the Crystal Form II of Dabrafenib methanesulfonate,
wherein the amount of the Crystal Form IV of Dabrafenib methanesulfonate is 1.1 to 20 times of its solubility in water at room temperature,
wherein the recrystallizing temperature is room temperature to 40° C.,
and wherein the duration of recrystallizing is 0.5 to 25 minutes.

5. A Crystal Form III of Dabrafenib methanesulfonate with the structural formula shown below,

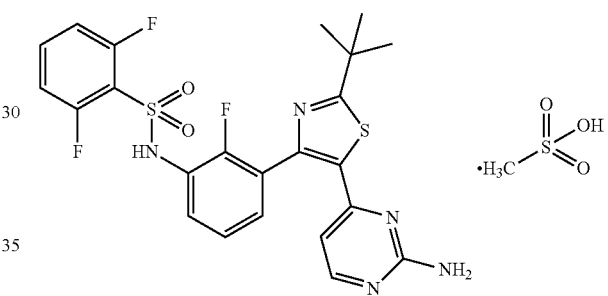

wherein the Crystal Form III of Dabrafenib methanesulfonate is characterized by a X-ray powder diffraction pattern measured using Cu-Kα radiation having the characteristic peaks at the diffraction angles 2θ of 4.2±0.2°, 8.6±0.2°, 13.2±0.2°, 14.5±0.2°, 17.4±0.2° and 19.5±0.2°.

6. The crystal Form III of Dabrafenib methanesulfonate according to claim 5, wherein the crystal Form III of Dabrafenib methanesulfonate is characterized by a X-ray powder diffraction pattern having the characteristic peaks at the diffraction angles 2θ of 4.2±0.2°, 8.6±0.2°, 12.4±0.2°, 13.2±0.2°, 14.5±0.2°, 17.4±0.2°, 18.0=0.2°, 18.6±0.2°, 19.5±0.2°, 20.1±0.2°, 24.7±0.2° and 25.1±0.2°.

7. The Crystal Form III of Dabrafenib methanesulfonate according to claim 6, wherein the crystal Form III of Dabrafenib methanesulfonate is characterized by a X-ray powder diffraction pattern having the following characteristic peaks at the diffraction angles 2θ and their relative intensities:

| Diffraction angle 2θ | Relative intensity % |
|---|---|
| 4.2 ± 0.2° | 25.5 |
| 8.6 ± 0.2° | 100.0 |
| 9.6 ± 0.2° | 20.7 |
| 12.4 ± 0.2° | 30.5 |
| 13.2 ± 0.2° | 90.5 |
| 14.5 ± 0.2° | 52.4 |
| 16.4 ± 0.2° | 21.5 |
| 17.4 ± 0.2° | 41.5 |

-continued

| Diffraction angle 2θ | Relative intensity % |
|---|---|
| 18.0 ± 0.2° | 26.5 |
| 18.6 ± 0.2° | 33.1 |
| 19.5 ± 0.2° | 59.3 |
| 20.1 ± 0.2° | 45.1 |
| 21.8 ± 0,2° | 17.5 |
| 23.2 ± 0.2° | 21.1 |
| 24.7 ± 0.2° | 44.4 |
| 25.1 ± 0.2° | 33.8 |
| 28.7 ± 0.2° | 22.5. |

8. A method of preparing the Crystal Form III of Dabrafenib methanesulfonate according to claim 5, comprising: dissolving known Crystal Form I of Dabrafenib methanesulfonate into a mixed solvent of methanol and an organic solvent, evaporating to crystallize, then separating the precipitated crystals, without drying to get the Crystal Form III of Dabrafenib methanesulfonate;
wherein the organic solvent is selected from the group consisting of ethyl ethyl acetate, butanone and $C_4$-alkanol;
wherein the amount of the known Crystal Form of Dabrafenib methanesulfonate is 0.1 to 1 times of its solubility in the mixed solvent at room temperature;
wherein the volume ratio of methanol to the organic solvent is 0.1:1 to 100:1;
wherein the crystallizing temperature is room temperature to 40° C.;
and wherein the duration of crystallization is 1 to 60 minutes.

9. A Crystal Form V of Dabrafenib methanesulfonate with the structural formula shown below,

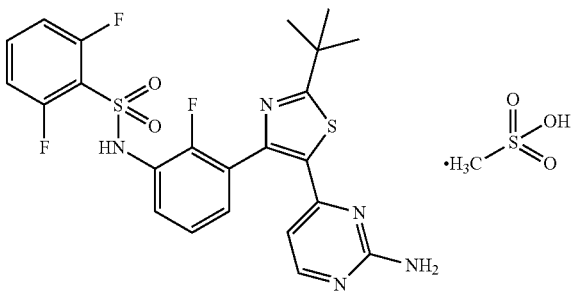

wherein the Crystal Form V of Dabrafenib methanesulfonate is characterized by a X-ray powder diffraction pattern measured using Cu-Kα radiation having the characteristic peaks at the diffraction angles 2θ of 8.9±0.2°, 14.8±0.2°, 15.8±0.2°, 16.7±0.2°, 17.9±0.2° and 19.0±0.2°.

10. The Crystal Form V of Dabrafenib methanesulfonate according to claim 9, wherein the Crystal Form V of Dabrafenib methanesulfonate is characterized by a X-ray powder diffraction pattern having the characteristic peaks at the diffraction angles 2θ of 8.9±0.2°, 14.8±0.2°, 15.1±0.2°, 15.8±0.2°, 16.7±0.2°, 17.9±0.2°, 19.0±0.2°, 23.8±0.2°, 25.5±0.2°, 31.1±0.2< and 36.1±0.2°.

11. The Crystal Form V of Dabrafenib methanesulfonate according to claim 10, wherein the Crystal Form V of Dabrafenib methanesulfonate is characterized by a X-ray powder diffraction pattern having the following characteristic peaks at the diffraction angles 2θ and their relative intensities:

| Diffraction angle 2θ | Relative intensity % |
|---|---|
| 8.9 ± 0.2° | 100.0 |
| 14.8 ± 0.2° | 31.7 |
| 15.1 ± 0.2° | 10.2 |
| 15.8 ± 0.2° | 35.6 |
| 16.7 ± 0.2° | 15.5 |
| 17.9 ± 0.2° | 31.7 |
| 19.0 ± 0.2° | 29.2 |
| 23.8 ± 0.2° | 25.3 |
| 25.5 ± 0.2° | 20.2 |
| 31.1 ± 0.2° | 65.0 |
| 36.1 ± 0.2° | 28.7. |

12. A method of preparing the Crystal Form V of Dabrafenib methanesulfonate according to claim 9, comprising: storing Crystal Form IV of Dabrafenib methanesulfonate at a high temperature for a period of time to get the Crystal Form V of Dabrafenib methanesulfonate;
wherein the high temperature is 40° C. to 120° C.; the duration of storage is 0.1 to 2 hours.

13. A pharmaceutical composition, comprising a therapeutically effective amount of the Crystal Form II of Dabrafenib methanesulfonate according to claim 1 and at least one pharmaceutical acceptable excipient.

14. The pharmaceutical composition according to claim 13, wherein the pharmaceutical composition is in a dosage form selected from the group consisting of tablets, capsules, suspensions, disintegrating tablets, immediate release tablets, slow release tablets and controlled release tablets.

15. A method of treating the diseases associated with one or more Raf-family kinases, comprises administering to a mammalian subject in need thereof a therapeutically effective amount of the pharmaceutical composition according to claim 13.

16. A method of treating cancer by inhibition of one or more Raf-family kinases, comprises administering to a mammalian subject in need thereof a therapeutically effective amount of the pharmaceutical composition according to claim 13.

17. The method of claim 16, wherein the cancer is melanoma.

18. The method of claim 16, wherein the cancer is selected from the group consisting of Barret's adenocarcinoma, biliary tract carcinoma, breast cancer, cervical carcinoma, cholangiocarcinoma, central nervous system tumors, colorectal cancer, gastric carcinoma, head and neck cancer, leukemia, lymphoma, myelodysplastic syndrome, chronic myeloid leukemia, Hodgkin's lymphoma, non Hodgkin's lymphoma, megakaryocytic leukemia, multiple myeloma, erythroleukemia, hepatocellular carcinoma, small cell lung cancer, non-small cell lung cancer, ovarian cancer, endometrial carcinoma, pancreatic cancer, pituitary adenoma, prostate cancer, renal carcinoma, sarcoma, and thyroid carcinoma.

19. A pharmaceutical composition, comprising a therapeutically effective amount of the Crystal Form III of Dabrafenib methanesulfonate according to claim 5 and at least one pharmaceutical acceptable excipient.

20. A pharmaceutical composition, comprising a therapeutically effective amount of the Crystal Form V of Dabrafenib methanesulfonate according to claim 9 and at least one pharmaceutical acceptable excipient.

* * * * *